(12) United States Patent
Huh et al.

(10) Patent No.: US 8,951,769 B2
(45) Date of Patent: Feb. 10, 2015

(54) ENGINEERED DEMETER 5-METHYLCYTOSINE DNA GLYOSYLASE WITH IMPROVED YIELD, STABILITY AND SOLUBILITY

(75) Inventors: Jin Hoe Huh, Davis, CA (US); Robert Fischer, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 253 days.

(21) Appl. No.: 13/265,533

(22) PCT Filed: Apr. 19, 2010

(86) PCT No.: PCT/US2010/031623
§ 371 (c)(1),
(2), (4) Date: Jan. 3, 2012

(87) PCT Pub. No.: WO2010/123827
PCT Pub. Date: Oct. 28, 2010

(65) Prior Publication Data
US 2012/0149023 A1  Jun. 14, 2012

Related U.S. Application Data

(60) Provisional application No. 61/170,978, filed on Apr. 20, 2009.

(51) Int. Cl.
*C12N 9/24* (2006.01)
*C12Q 1/68* (2006.01)
*C12N 9/42* (2006.01)

(52) U.S. Cl.
CPC ............ *C12Q 1/6844* (2013.01); *C12N 9/2434* (2013.01); *C12N 9/2497* (2013.01)
USPC ........................................................ 435/200

(58) Field of Classification Search
None
See application file for complete search history.

(56) References Cited

U.S. PATENT DOCUMENTS

| 2003/0135890 | A1 | 7/2003 | Fischer et al. |
| 2006/0052291 | A1 | 3/2006 | Siegal et al. |
| 2009/0305241 | A1* | 12/2009 | Fischer et al. .................... 435/6 |

OTHER PUBLICATIONS

Hope et al., "Structural and functional characterization of the short acidic transcriptional activation region of yeast GCN4 protein", Nature 333:635-640, 1988.*
Mok et al.; "Domain structure of the Demeter 5-methylcytosine DNA glycosylase"; *Proc. Natl. Acad. Sci. USA*; 107(45):19225-19230 (Nov. 2010).
Supplementary European Search Report from EP 10767592.8, mailed Oct. 5, 2012 (6 pages).
International Search Report and Written Opinion dated Jul. 2, 2010, issued in related International Patent Application No. PCT/US2010/031623, filed Apr. 19, 2010.
Morales-Ruiz et al., *Demeter* and *Repressor of Silencing 1* encode 5-methylcytosine DNA glycosylases, 2006, Proc. Nat. Acad. Sci., vol. 103, No. 18, pp. 6853-6858.
Gehring et al., "Demeter DNA glycosylase establishes MEDEA polycomb gene self-imprinting by allele-specific demethylation," 2006, Cell, vol. 124, No. 3, pp. 495-506.
UNIPROTKB. Locus DME_ARATH, accession Q8LK56, Jun. 13, 2006 [online]. Retrieved Jun. 13, 2010]. Retrieved from the internet; <URL: http://www.ncbi.nlm.nih.gov/protein/108935833 >.

* cited by examiner

*Primary Examiner* — David J Steadman
(74) *Attorney, Agent, or Firm* — Kilpatrick Townsend & Stockton LLP

(57) ABSTRACT

Improved active DEMETER polypeptides with internal deletions are provided.

15 Claims, 5 Drawing Sheets

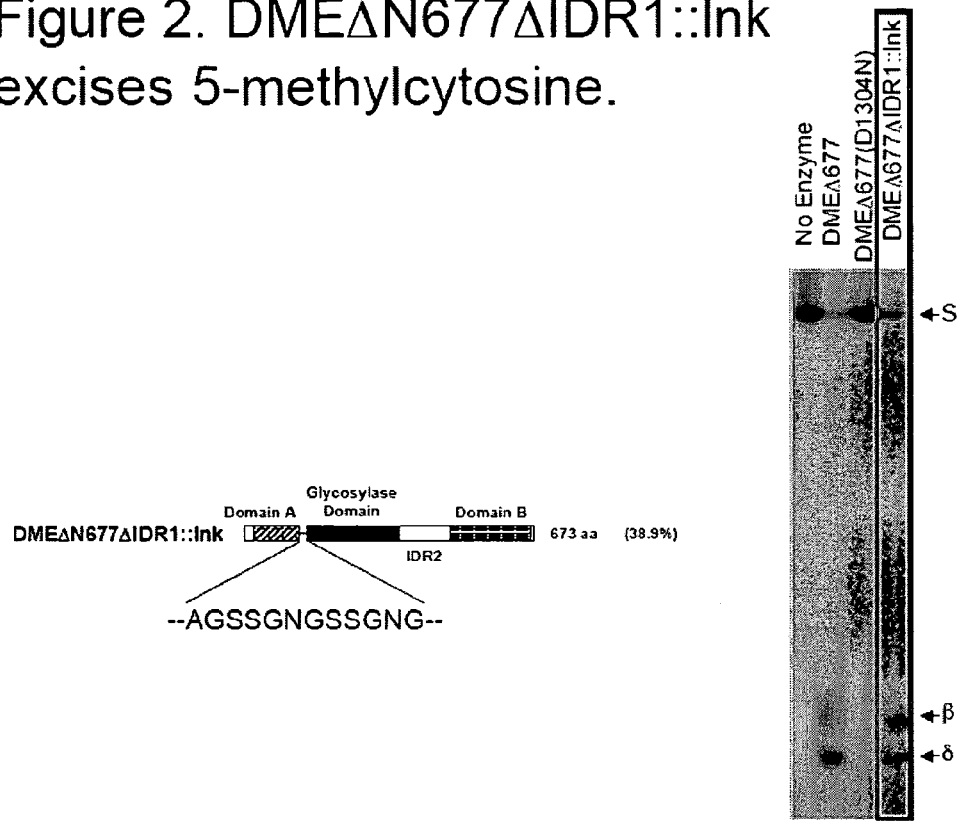
Figure 2. DMEΔN677ΔIDR1::lnk excises 5-methylcytosine.

Figure 3. Expression DMEΔN677ΔIDR1::lnk fusion proteins in E. coli
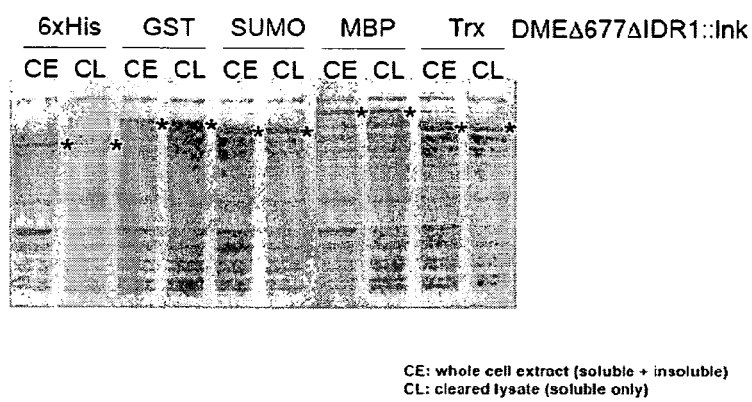

Figure 4. Purification of 6xHis-DMEΔN677ΔIDR1::lnk
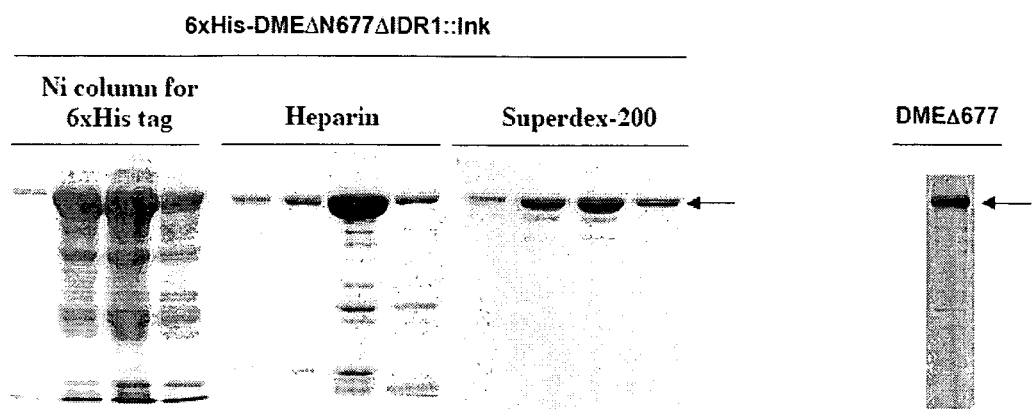

Figure 5. Properties of of different DME Polypeptides
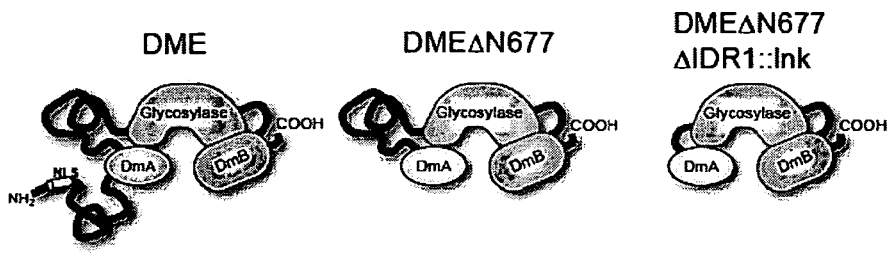
| Size (aa) | 1,729 | 1,052 | 673 |
|---|---|---|---|
| Activity* | Yes | Yes | Yes |
| Expression** | poor | moderate | good |
| Solubility* | n/a | poor | good |
| Stability* | n/a | moderate | good |
*in vitro   **in E. coli

SEQUENCE LISTING

```
<160> NUMBER OF SEQ ID NOS: 15

<210> SEQ ID NO 1
<211> LENGTH: 120
<212> TYPE: PRT
<213> ORGANISM: Arabidopsis thaliana
<220> FEATURE:
<223> OTHER INFORMATION: peptide encoded by positions 678 to 797 of
      DEMETER (DME, DMT, Atropos (ATR)) gene, demethylase, apurinic/
      apyrimidinic (AP) lyase, including conserved Domain A

<400> SEQUENCE: 1

Tyr Lys Gly Asp Gly Ala Leu Val Pro Tyr Glu Ser Lys Lys Arg Lys
 1               5                  10                  15

Pro Arg Pro Lys Val Asp Ile Asp Asp Glu Thr Thr Arg Ile Trp Asn
             20                  25                  30

Leu Leu Met Gly Lys Gly Asp Glu Lys Glu Gly Asp Glu Glu Lys Asp
         35                  40                  45
```

```
Lys Lys Lys Glu Lys Trp Trp Glu Glu Arg Arg Val Phe Arg Gly
     50              55                  60
Arg Ala Asp Ser Phe Ile Ala Arg Met His Leu Val Gln Gly Asp Arg
 65              70                  75                  80
Arg Phe Ser Pro Trp Lys Gly Ser Val Val Asp Ser Val Ile Gly Val
                 85                  90                  95
Phe Leu Thr Gln Asn Val Ser Asp His Leu Ser Ser Ser Ala Phe Met
             100                 105                 110
Ser Leu Ala Ala Arg Phe Pro Pro
             115                 120
```

<210> SEQ ID NO 2
<211> LENGTH: 541
<212> TYPE: PRT
<213> ORGANISM: Arabidopsis thaliana
<220> FEATURE:
<223> OTHER INFORMATION: peptide encoded by positions 1189 to 1729 of DEMETER (DME, DMT, Atropos (ATR)) gene, demethylase, apurinic/apyrimidinic (AP) lyase, including glycosylase domain, interdomain region 2 (IDR2) and conserved Domain B

<400> SEQUENCE: 2

```
Thr Ser Gln Trp Asp Ser Leu Arg Lys Asp Val Glu Gly Asn Glu Gly
 1               5                  10                  15
Arg Gln Glu Arg Asn Lys Asn Asn Met Asp Ser Ile Asp Tyr Glu Ala
             20                  25                  30
Ile Arg Arg Ala Ser Ile Ser Glu Ile Ser Glu Ala Ile Lys Glu Arg
         35                  40                  45
Gly Met Asn Asn Met Leu Ala Val Arg Ile Lys Asp Phe Leu Glu Arg
 50                  55                  60
Ile Val Lys Asp His Gly Gly Ile Asp Leu Glu Trp Leu Arg Glu Ser
 65              70                  75                  80
Pro Pro Asp Lys Ala Lys Asp Tyr Leu Leu Ser Ile Arg Gly Leu Gly
                 85                  90                  95
Leu Lys Ser Val Glu Cys Val Arg Leu Leu Thr Leu His Asn Leu Ala
             100                 105                 110
Phe Pro Val Asp Thr Asn Val Gly Arg Ile Ala Val Arg Met Gly Trp
             115                 120                 125
Val Pro Leu Gln Pro Leu Pro Glu Ser Leu Gln Leu His Leu Leu Glu
130                 135                 140
Leu Tyr Pro Val Leu Glu Ser Ile Gln Lys Phe Leu Trp Pro Arg Leu
145                 150                 155                 160
Cys Lys Leu Asp Gln Arg Thr Leu Tyr Glu Leu His Tyr Gln Leu Ile
                165                 170                 175
Thr Phe Gly Lys Val Phe Cys Thr Lys Ser Arg Pro Asn Cys Asn Ala
            180                 185                 190
Cys Pro Met Arg Gly Glu Cys Arg His Phe Ala Ser Ala Tyr Ala Ser
            195                 200                 205
Ala Arg Leu Ala Leu Pro Ala Pro Glu Glu Arg Ser Leu Thr Ser Ala
            210                 215                 220
Thr Ile Pro Val Pro Pro Glu Ser Phe Pro Pro Val Ala Ile Pro Met
225                 230                 235                 240
Ile Glu Leu Pro Leu Pro Leu Glu Lys Ser Leu Ala Ser Gly Ala Pro
                245                 250                 255
Ser Asn Arg Glu Asn Cys Glu Pro Ile Ile Glu Glu Pro Ala Ser Pro
            260                 265                 270
```

Gly Gln Glu Cys Thr Glu Ile Thr Glu Ser Asp Ile Glu Asp Ala Tyr
            275                 280                 285

Tyr Asn Glu Asp Pro Asp Glu Ile Pro Thr Ile Lys Leu Asn Ile Glu
        290                 295                 300

Gln Phe Gly Met Thr Leu Arg Glu His Met Glu Arg Asn Met Glu Leu
305                 310                 315                 320

Gln Glu Gly Asp Met Ser Lys Ala Leu Val Ala Leu His Pro Thr Thr
                325                 330                 335

Thr Ser Ile Pro Thr Pro Lys Leu Lys Asn Ile Ser Arg Leu Arg Thr
            340                 345                 350

Glu His Gln Val Tyr Glu Leu Pro Asp Ser His Arg Leu Leu Asp Gly
        355                 360                 365

Met Asp Lys Arg Glu Pro Asp Asp Pro Ser Pro Tyr Leu Leu Ala Ile
370                 375                 380

Trp Thr Pro Gly Glu Thr Ala Asn Ser Ala Gln Pro Pro Glu Gln Lys
385                 390                 395                 400

Cys Gly Gly Lys Ala Ser Gly Lys Met Cys Phe Asp Glu Thr Cys Ser
                405                 410                 415

Glu Cys Asn Ser Leu Arg Glu Ala Asn Ser Gln Thr Val Arg Gly Thr
            420                 425                 430

Leu Leu Ile Pro Cys Arg Thr Ala Met Arg Gly Ser Phe Pro Leu Asn
        435                 440                 445

Gly Thr Tyr Phe Gln Val Asn Glu Leu Phe Ala Asp His Glu Ser Ser
450                 455                 460

Leu Lys Pro Ile Asp Val Pro Arg Asp Trp Ile Trp Asp Leu Pro Arg
465                 470                 475                 480

Arg Thr Val Tyr Phe Gly Thr Ser Val Thr Ser Ile Phe Arg Gly Leu
                485                 490                 495

Ser Thr Glu Gln Ile Gln Phe Cys Phe Trp Lys Gly Phe Val Cys Val
            500                 505                 510

Arg Gly Phe Glu Gln Lys Thr Arg Ala Pro Arg Pro Leu Met Ala Arg
        515                 520                 525

Leu His Phe Pro Ala Ser Lys Leu Lys Asn Asn Lys Thr
530                 535                 540

<210> SEQ ID NO 3
<211> LENGTH: 391
<212> TYPE: PRT
<213> ORGANISM: Arabidopsis thaliana
<220> FEATURE:
<223> OTHER INFORMATION: peptide encoded by positions 798 to 1188 of
      DEMETER (DME, DMT, Atropos (ATR)) gene, demethylase, apurinic/
      apyrimidinic (AP) lyase, deleted interdomain region 1 (IDR1)

<400> SEQUENCE: 3

Lys Leu Ser Ser Ser Arg Glu Asp Glu Arg Asn Val Arg Ser Val Val
1               5                   10                  15

Val Glu Asp Pro Glu Gly Cys Ile Leu Asn Leu Asn Glu Ile Pro Ser
            20                  25                  30

Trp Gln Glu Lys Val Gln His Pro Ser Asp Met Glu Val Ser Gly Val
        35                  40                  45

Asp Ser Gly Ser Lys Glu Gln Leu Arg Asp Cys Ser Asn Ser Gly Ile
    50                  55                  60

Glu Arg Phe Asn Phe Leu Glu Lys Ser Ile Gln Asn Leu Glu Glu Glu
65                  70                  75                  80

```
Val Leu Ser Ser Gln Asp Ser Phe Asp Pro Ala Ile Phe Gln Ser Cys
                85                  90                  95

Gly Arg Val Gly Ser Cys Ser Cys Ser Lys Ser Asp Ala Glu Phe Pro
            100                 105                 110

Thr Thr Arg Cys Glu Thr Lys Thr Val Ser Gly Thr Ser Gln Ser Val
        115                 120                 125

Gln Thr Gly Ser Pro Asn Leu Ser Asp Glu Ile Cys Leu Gln Gly Asn
    130                 135                 140

Glu Arg Pro His Leu Tyr Glu Gly Ser Gly Asp Val Gln Lys Gln Glu
145                 150                 155                 160

Thr Thr Asn Val Ala Gln Lys Lys Pro Asp Leu Glu Lys Thr Met Asn
                165                 170                 175

Trp Lys Asp Ser Val Cys Phe Gly Gln Pro Arg Asn Asp Thr Asn Trp
            180                 185                 190

Gln Thr Thr Pro Ser Ser Ser Tyr Glu Gln Cys Ala Thr Arg Gln Pro
        195                 200                 205

His Val Leu Asp Ile Glu Asp Phe Gly Met Gln Gly Glu Gly Leu Gly
    210                 215                 220

Tyr Ser Trp Met Ser Ile Ser Pro Arg Val Asp Arg Val Lys Asn Lys
225                 230                 235                 240

Asn Val Pro Arg Arg Phe Phe Arg Gln Gly Gly Ser Val Pro Arg Glu
                245                 250                 255

Phe Thr Gly Gln Ile Ile Pro Ser Thr Pro His Glu Leu Pro Gly Met
            260                 265                 270

Gly Leu Ser Gly Ser Ser Ala Val Gln Glu His Gln Asp Asp Thr
        275                 280                 285

Gln His Asn Gln Gln Asp Glu Met Asn Lys Ala Ser His Leu Gln Lys
    290                 295                 300

Thr Phe Leu Asp Leu Leu Asn Ser Ser Glu Glu Cys Leu Thr Arg Gln
305                 310                 315                 320

Ser Ser Thr Lys Gln Asn Ile Thr Asp Gly Cys Leu Pro Arg Asp Arg
                325                 330                 335

Thr Ala Glu Asp Val Val Asp Pro Leu Ser Asn Asn Ser Ser Leu Gln
            340                 345                 350

Asn Ile Leu Val Glu Ser Asn Ser Ser Asn Lys Glu Gln Thr Ala Val
        355                 360                 365

Glu Tyr Lys Glu Thr Asn Ala Thr Ile Leu Arg Glu Met Lys Gly Thr
    370                 375                 380

Leu Ala Asp Gly Lys Lys Pro
385                 390

<210> SEQ ID NO 4
<211> LENGTH: 12
<212> TYPE: PRT
<213> ORGANISM: Artificial Sequence
<220> FEATURE:
<223> OTHER INFORMATION: synthetic short linker peptide lnk,
      heterologous linker

<400> SEQUENCE: 4

Ala Gly Ser Ser Gly Asn Gly Ser Ser Gly Asn Gly
  1               5                  10

<210> SEQ ID NO 5
<211> LENGTH: 1729
<212> TYPE: PRT
<213> ORGANISM: Arabidopsis thaliana
```

```
<220> FEATURE:
<223> OTHER INFORMATION: amino acid sequence of gene DME
<220> FEATURE:
<223> OTHER INFORMATION: DEMETER DNA glycosylase (DME, DMT, Atropos
      (ATR)), demethylase, apurinic/apyrimidinic (AP) lyase
<220> FEATURE:
<221> NAME/KEY: DOMAIN
<222> LOCATION: (1167)...(1368)
<223> OTHER INFORMATION: DNA glycolase domain

<400> SEQUENCE: 5
```

Met Gln Ser Ile Met Asp Ser Ser Ala Val Asn Ala Thr Glu Ala Thr
 1               5                  10                  15

Glu Gln Asn Asp Gly Ser Arg Gln Asp Val Leu Glu Phe Asp Leu Asn
            20                  25                  30

Lys Thr Pro Gln Gln Lys Pro Ser Lys Arg Lys Arg Lys Phe Met Pro
        35                  40                  45

Lys Val Val Glu Gly Lys Pro Arg Lys Pro Arg Lys Pro Ala
    50                  55                  60

Glu Leu Pro Lys Val Val Glu Gly Lys Pro Lys Arg Lys Pro Arg
65                  70                  75                  80

Lys Ala Ala Thr Gln Glu Lys Val Lys Ser Lys Glu Thr Gly Ser Ala
                85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190

Pro Leu Glu Val Ser Met Gly Asn Gln Pro Asp Lys Leu Ser Thr Gly
        195                 200                 205

Ala Lys Leu Ala Arg Asp Gln Gln Pro Asp Leu Leu Thr Arg Asn Gln
210                 215                 220

Gln Cys Gln Phe Pro Val Ala Thr Gln Asn Thr Gln Phe Pro Met Glu
225                 230                 235                 240

Asn Gln Gln Ala Trp Leu Gln Met Lys Asn Gln Leu Ile Gly Phe Pro
                245                 250                 255

Phe Gly Asn Gln Gln Pro Arg Met Thr Ile Arg Asn Gln Gln Pro Cys
            260                 265                 270

Leu Ala Met Gly Asn Gln Gln Pro Met Tyr Leu Ile Gly Thr Pro Arg
        275                 280                 285

Pro Ala Leu Val Ser Gly Asn Gln Leu Gly Gly Pro Gln Gly Asn
290                 295                 300

Lys Arg Pro Ile Phe Leu Asn His Gln Thr Cys Leu Pro Ala Gly Asn
305                 310                 315                 320

Gln Leu Tyr Gly Ser Pro Thr Asp Met His Gln Leu Val Met Ser Thr
                325                 330                 335

Gly Gly Gln Gln His Gly Leu Leu Ile Lys Asn Gln Gln Pro Gly Ser
            340                 345                 350

```
Leu Ile Arg Gly Gln Gln Pro Cys Val Pro Leu Ile Asp Gln Gln Pro
            355                 360                 365

Ala Thr Pro Lys Gly Phe Thr His Leu Asn Gln Met Val Ala Thr Ser
370                 375                 380

Met Ser Ser Pro Gly Leu Arg Pro His Ser Gln Ser Gln Val Pro Thr
385                 390                 395                 400

Thr Tyr Leu His Val Glu Ser Val Ser Arg Ile Leu Asn Gly Thr Thr
                405                 410                 415

Gly Thr Cys Gln Arg Ser Arg Ala Pro Ala Tyr Asp Ser Leu Gln Gln
            420                 425                 430

Asp Ile His Gln Gly Asn Lys Tyr Ile Leu Ser His Glu Ile Ser Asn
        435                 440                 445

Gly Asn Gly Cys Lys Lys Ala Leu Pro Gln Asn Ser Ser Leu Pro Thr
    450                 455                 460

Pro Ile Met Ala Lys Leu Glu Glu Ala Arg Gly Ser Lys Arg Gln Tyr
465                 470                 475                 480

His Arg Ala Met Gly Gln Thr Glu Lys His Asp Leu Asn Leu Ala Gln
                485                 490                 495

Gln Ile Ala Gln Ser Gln Asp Val Glu Arg His Asn Ser Ser Thr Cys
            500                 505                 510

Val Glu Tyr Leu Asp Ala Ala Lys Lys Thr Lys Ile Gln Lys Val Val
        515                 520                 525

Gln Glu Asn Leu His Gly Met Pro Pro Glu Val Ile Glu Ile Glu Asp
    530                 535                 540

Asp Pro Thr Asp Gly Ala Arg Lys Gly Lys Asn Thr Ala Ser Ile Ser
545                 550                 555                 560

Lys Gly Ala Ser Lys Gly Asn Ser Ser Pro Val Lys Lys Thr Ala Glu
                565                 570                 575

Lys Glu Lys Cys Ile Val Pro Lys Thr Pro Ala Lys Lys Gly Arg Ala
            580                 585                 590

Gly Arg Lys Lys Ser Val Pro Pro Ala His Ala Ser Glu Ile Gln
        595                 600                 605

Leu Trp Gln Pro Thr Pro Pro Lys Thr Pro Leu Ser Arg Ser Lys Pro
    610                 615                 620

Lys Gly Lys Gly Arg Lys Ser Ile Gln Asp Ser Gly Lys Ala Arg Gly
625                 630                 635                 640

Pro Ser Gly Glu Leu Leu Cys Gln Asp Ser Ile Ala Glu Ile Ile Tyr
                645                 650                 655

Arg Met Gln Asn Leu Tyr Leu Gly Asp Lys Glu Arg Glu Gln Glu Gln
            660                 665                 670

Asn Ala Met Val Leu Tyr Lys Gly Asp Gly Ala Leu Val Pro Tyr Glu
        675                 680                 685

Ser Lys Lys Arg Lys Pro Arg Pro Lys Val Asp Ile Asp Asp Glu Thr
    690                 695                 700

Thr Arg Ile Trp Asn Leu Leu Met Gly Lys Gly Asp Glu Lys Glu Gly
705                 710                 715                 720

Asp Glu Glu Lys Asp Lys Lys Glu Lys Trp Trp Glu Glu Arg
                725                 730                 735

Arg Val Phe Arg Gly Arg Ala Asp Ser Phe Ile Ala Arg Met His Leu
            740                 745                 750

Val Gln Gly Asp Arg Arg Phe Ser Pro Trp Lys Gly Ser Val Val Asp
        755                 760                 765
```

-continued

Ser Val Ile Gly Val Phe Leu Thr Gln Asn Val Ser Asp His Leu Ser
770             775                 780

Ser Ser Ala Phe Met Ser Leu Ala Ala Arg Phe Pro Pro Lys Leu Ser
785             790                 795                 800

Ser Ser Arg Glu Asp Glu Arg Asn Val Arg Ser Val Val Glu Asp
            805                 810                 815

Pro Glu Gly Cys Ile Leu Asn Leu Asn Glu Ile Pro Ser Trp Gln Glu
            820                 825                 830

Lys Val Gln His Pro Ser Asp Met Glu Val Ser Gly Val Asp Ser Gly
            835                 840                 845

Ser Lys Glu Gln Leu Arg Asp Cys Ser Asn Ser Gly Ile Glu Arg Phe
850                 855                 860

Asn Phe Leu Glu Lys Ser Ile Gln Asn Leu Glu Glu Glu Val Leu Ser
865                 870                 875                 880

Ser Gln Asp Ser Phe Asp Pro Ala Ile Phe Gln Ser Cys Gly Arg Val
                885                 890                 895

Gly Ser Cys Ser Cys Ser Lys Ser Asp Ala Glu Phe Pro Thr Thr Arg
            900                 905                 910

Cys Glu Thr Lys Thr Val Ser Gly Thr Ser Gln Ser Val Gln Thr Gly
            915                 920                 925

Ser Pro Asn Leu Ser Asp Glu Ile Cys Leu Gln Gly Asn Glu Arg Pro
930                 935                 940

His Leu Tyr Glu Gly Ser Gly Asp Val Gln Lys Gln Glu Thr Thr Asn
945                 950                 955                 960

Val Ala Gln Lys Lys Pro Asp Leu Glu Lys Thr Met Asn Trp Lys Asp
                965                 970                 975

Ser Val Cys Phe Gly Gln Pro Arg Asn Asp Thr Asn Trp Gln Thr Thr
            980                 985                 990

Pro Ser Ser Ser Tyr Glu Gln Cys Ala Thr Arg Gln Pro His Val Leu
            995                 1000                1005

Asp Ile Glu Asp Phe Gly Met Gln Gly Glu Gly Leu Gly Tyr Ser Trp
            1010                1015                1020

Met Ser Ile Ser Pro Arg Val Asp Arg Val Lys Asn Lys Asn Val Pro
1025                1030                1035                1040

Arg Arg Phe Phe Arg Gln Gly Gly Ser Val Pro Arg Glu Phe Thr Gly
                1045                1050                1055

Gln Ile Ile Pro Ser Thr Pro His Glu Leu Pro Gly Met Gly Leu Ser
            1060                1065                1070

Gly Ser Ser Ser Ala Val Gln Glu His Gln Asp Asp Thr Gln His Asn
            1075                1080                1085

Gln Gln Asp Glu Met Asn Lys Ala Ser His Leu Gln Lys Thr Phe Leu
            1090                1095                1100

Asp Leu Leu Asn Ser Ser Glu Glu Cys Leu Thr Arg Gln Ser Ser Thr
1105                1110                1115                1120

Lys Gln Asn Ile Thr Asp Gly Cys Leu Pro Arg Asp Arg Thr Ala Glu
                1125                1130                1135

Asp Val Val Asp Pro Leu Ser Asn Asn Ser Ser Leu Gln Asn Ile Leu
            1140                1145                1150

Val Glu Ser Asn Ser Ser Asn Lys Glu Gln Thr Ala Val Glu Tyr Lys
            1155                1160                1165

Glu Thr Asn Ala Thr Ile Leu Arg Glu Met Lys Gly Thr Leu Ala Asp
            1170                1175                1180

-continued

```
Gly Lys Lys Pro Thr Ser Gln Trp Asp Ser Leu Arg Lys Asp Val Glu
1185                1190                1195                1200

Gly Asn Glu Gly Arg Gln Glu Arg Asn Lys Asn Asn Met Asp Ser Ile
            1205                1210                1215

Asp Tyr Glu Ala Ile Arg Arg Ala Ser Ile Ser Glu Ile Ser Glu Ala
            1220                1225                1230

Ile Lys Glu Arg Gly Met Asn Met Leu Ala Val Arg Ile Lys Asp
        1235                1240                1245

Phe Leu Glu Arg Ile Val Lys Asp His Gly Gly Ile Asp Leu Glu Trp
    1250                1255                1260

Leu Arg Glu Ser Pro Pro Asp Lys Ala Lys Asp Tyr Leu Leu Ser Ile
1265                1270                1275                1280

Arg Gly Leu Gly Leu Lys Ser Val Glu Cys Val Arg Leu Leu Thr Leu
                1285                1290                1295

His Asn Leu Ala Phe Pro Val Asp Thr Asn Val Gly Arg Ile Ala Val
            1300                1305                1310

Arg Met Gly Trp Val Pro Leu Gln Pro Leu Pro Glu Ser Leu Gln Leu
            1315                1320                1325

His Leu Leu Glu Leu Tyr Pro Val Leu Glu Ser Ile Gln Lys Phe Leu
        1330                1335                1340

Trp Pro Arg Leu Cys Lys Leu Asp Gln Arg Thr Leu Tyr Glu Leu His
1345                1350                1355                1360

Tyr Gln Leu Ile Thr Phe Gly Lys Val Phe Cys Thr Lys Ser Arg Pro
            1365                1370                1375

Asn Cys Asn Ala Cys Pro Met Arg Gly Glu Cys Arg His Phe Ala Ser
            1380                1385                1390

Ala Tyr Ala Ser Ala Arg Leu Ala Leu Pro Ala Pro Glu Glu Arg Ser
        1395                1400                1405

Leu Thr Ser Ala Thr Ile Pro Val Pro Pro Glu Ser Phe Pro Pro Val
    1410                1415                1420

Ala Ile Pro Met Ile Glu Leu Pro Leu Pro Leu Glu Lys Ser Leu Ala
1425                1430                1435                1440

Ser Gly Ala Pro Ser Asn Arg Glu Asn Cys Glu Pro Ile Ile Glu Glu
                1445                1450                1455

Pro Ala Ser Pro Gly Gln Glu Cys Thr Glu Ile Thr Glu Ser Asp Ile
            1460                1465                1470

Glu Asp Ala Tyr Tyr Asn Glu Asp Pro Asp Glu Ile Pro Thr Ile Lys
            1475                1480                1485

Leu Asn Ile Glu Gln Phe Gly Met Thr Leu Arg Glu His Met Glu Arg
        1490                1495                1500

Asn Met Glu Leu Gln Glu Gly Asp Met Ser Lys Ala Leu Val Ala Leu
1505                1510                1515                1520

His Pro Thr Thr Thr Ser Ile Pro Thr Pro Lys Leu Lys Asn Ile Ser
                1525                1530                1535

Arg Leu Arg Thr Glu His Gln Val Tyr Glu Leu Pro Asp Ser His Arg
            1540                1545                1550

Leu Leu Asp Gly Met Asp Lys Arg Glu Pro Asp Asp Pro Ser Pro Tyr
        1555                1560                1565

Leu Leu Ala Ile Trp Thr Pro Gly Glu Thr Ala Asn Ser Ala Gln Pro
    1570                1575                1580

Pro Glu Gln Lys Cys Gly Gly Lys Ala Ser Gly Lys Met Cys Phe Asp
1585                1590                1595                1600
```

```
Glu Thr Cys Ser Glu Cys Asn Ser Leu Arg Glu Ala Asn Ser Gln Thr
                1605                1610                1615

Val Arg Gly Thr Leu Leu Ile Pro Cys Arg Thr Ala Met Arg Gly Ser
            1620                1625                1630

Phe Pro Leu Asn Gly Thr Tyr Phe Gln Val Asn Glu Leu Phe Ala Asp
            1635                1640                1645

His Glu Ser Ser Leu Lys Pro Ile Asp Val Pro Arg Asp Trp Ile Trp
        1650                1655                1660

Asp Leu Pro Arg Arg Thr Val Tyr Phe Gly Thr Ser Val Thr Ser Ile
1665                1670                1675                1680

Phe Arg Gly Leu Ser Thr Glu Gln Ile Gln Phe Cys Phe Trp Lys Gly
                1685                1690                1695

Phe Val Cys Val Arg Gly Phe Glu Gln Lys Thr Arg Ala Pro Arg Pro
            1700                1705                1710

Leu Met Ala Arg Leu His Phe Pro Ala Ser Lys Leu Lys Asn Asn Lys
            1715                1720                1725

Thr
```

<210> SEQ ID NO 6
<211> LENGTH: 1393
<212> TYPE: PRT
<213> ORGANISM: Arabidopsis thaliana
<220> FEATURE:
<223> OTHER INFORMATION: ROS1 DNA glycosylase, demethylase

<400> SEQUENCE: 6

```
Met Glu Lys Gln Arg Arg Glu Glu Ser Ser Phe Gln Gln Pro Pro Trp
1               5                   10                  15

Ile Pro Gln Thr Pro Met Lys Pro Phe Ser Pro Ile Cys Pro Tyr Thr
            20                  25                  30

Val Glu Asp Gln Tyr His Ser Ser Gln Leu Glu Glu Arg Arg Phe Val
        35                  40                  45

Gly Asn Lys Asp Met Ser Gly Leu Asp His Leu Ser Phe Gly Asp Leu
    50                  55                  60

Leu Ala Leu Ala Asn Thr Ala Ser Leu Ile Phe Ser Gly Gln Thr Pro
65                  70                  75                  80

Ile Pro Thr Arg Asn Thr Glu Val Met Gln Lys Gly Thr Glu Glu Val
                85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220
```

```
Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
            245                 250                 255

Pro Lys Lys Asn Gly Ser Asn Leu Glu Glu Val Asp Ile Ser Met Ala
        260                 265                 270

Gln Ala Ala Lys Arg Arg Gln Gly Pro Thr Cys Cys Asp Met Asn Leu
    275                 280                 285

Ser Gly Ile Gln Tyr Asp Glu Gln Cys Asp Tyr Gln Lys Met His Trp
290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
450                 455                 460

Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
                485                 490                 495

Pro Tyr Thr Met Asn Ser Gln Ile Val Leu Phe Gly Gly Ala Gly
            500                 505                 510

Ala Ile Val Pro Val Thr Pro Val Lys Lys Pro Arg Pro Arg Pro Lys
        515                 520                 525

Val Asp Leu Asp Asp Glu Thr Asp Arg Val Trp Lys Leu Leu Leu Glu
530                 535                 540

Asn Ile Asn Ser Glu Gly Val Asp Gly Ser Asp Glu Gln Lys Ala Lys
545                 550                 555                 560

Trp Trp Glu Glu Glu Arg Asn Val Phe Arg Gly Arg Ala Asp Ser Phe
                565                 570                 575

Ile Ala Arg Met His Leu Val Gln Gly Asp Arg Arg Phe Thr Pro Trp
            580                 585                 590

Lys Gly Ser Val Val Asp Ser Val Val Gly Val Phe Leu Thr Gln Asn
        595                 600                 605

Val Ser Asp His Leu Ser Ser Ala Phe Met Ser Leu Ala Ser Gln
610                 615                 620

Phe Pro Val Pro Phe Val Pro Ser Ser Asn Phe Asp Ala Gly Thr Ser
625                 630                 635                 640
```

-continued

```
Ser Met Pro Ser Ile Gln Ile Thr Tyr Leu Asp Ser Glu Glu Thr Met
            645                 650                 655

Ser Ser Pro Pro Asp His Asn His Ser Ser Val Thr Leu Lys Asn Thr
        660                 665                 670

Gln Pro Asp Glu Glu Lys Asp Tyr Val Pro Ser Asn Glu Thr Ser Arg
            675                 680                 685

Ser Ser Ser Glu Ile Ala Ile Ser Ala His Glu Ser Val Asp Lys Thr
    690                 695                 700

Thr Asp Ser Lys Glu Tyr Val Asp Ser Asp Arg Lys Gly Ser Ser Val
705                 710                 715                 720

Glu Val Asp Lys Thr Asp Glu Lys Cys Arg Val Leu Asn Leu Phe Pro
                725                 730                 735

Ser Glu Asp Ser Ala Leu Thr Cys Gln His Ser Met Val Ser Asp Ala
                740                 745                 750

Pro Gln Asn Thr Glu Arg Ala Gly Ser Ser Glu Ile Asp Leu Glu
            755                 760                 765

Gly Glu Tyr Arg Thr Ser Phe Met Lys Leu Leu Gln Gly Val Gln Val
    770                 775                 780

Ser Leu Glu Asp Ser Asn Gln Val Ser Pro Asn Met Ser Pro Gly Asp
785                 790                 795                 800

Cys Ser Ser Glu Ile Lys Gly Phe Gln Ser Met Lys Glu Pro Thr Lys
                805                 810                 815

Ser Ser Val Asp Ser Ser Glu Pro Gly Cys Cys Ser Gln Gln Asp Gly
                820                 825                 830

Asp Val Leu Ser Cys Gln Lys Pro Thr Leu Lys Glu Lys Gly Lys Lys
            835                 840                 845

Val Leu Lys Glu Glu Lys Lys Ala Phe Asp Trp Asp Cys Leu Arg Arg
850                 855                 860

Glu Ala Gln Ala Arg Ala Gly Ile Arg Glu Lys Thr Arg Ser Thr Met
865                 870                 875                 880

Asp Thr Val Asp Trp Lys Ala Ile Arg Ala Ala Asp Val Lys Glu Val
                885                 890                 895

Ala Glu Thr Ile Lys Ser Arg Gly Met Asn His Lys Leu Ala Glu Arg
            900                 905                 910

Ile Gln Gly Phe Leu Asp Arg Leu Val Asn Asp His Gly Ser Ile Asp
            915                 920                 925

Leu Glu Trp Leu Arg Asp Val Pro Pro Asp Lys Ala Lys Glu Tyr Leu
    930                 935                 940

Leu Ser Phe Asn Gly Leu Gly Leu Lys Ser Val Glu Cys Val Arg Leu
945                 950                 955                 960

Leu Thr Leu His His Leu Ala Phe Pro Val Asp Thr Asn Val Gly Arg
                965                 970                 975

Ile Ala Val Arg Leu Gly Trp Val Pro Leu Gln Pro Leu Pro Glu Ser
            980                 985                 990

Leu Gln Leu His Leu Leu Glu Met Tyr Pro Met Leu Glu Ser Ile Gln
        995                 1000                1005

Lys Tyr Leu Trp Pro Arg Leu Cys Lys Leu Asp Gln Lys Thr Leu Tyr
    1010                1015                1020

Glu Leu His Tyr Gln Met Ile Thr Phe Gly Lys Val Phe Cys Thr Lys
1025                1030                1035                1040

Ser Lys Pro Asn Cys Asn Ala Cys Pro Met Lys Gly Glu Cys Arg His
                1045                1050                1055
```

```
Phe Ala Ser Ala Phe Ala Ser Ala Arg Leu Ala Leu Pro Ser Thr Glu
            1060                1065                1070

Lys Gly Met Gly Thr Pro Asp Lys Asn Pro Leu Pro Leu His Leu Pro
        1075                1080                1085

Glu Pro Phe Gln Arg Glu Gln Gly Ser Glu Val Val Gln His Ser Glu
    1090                1095                1100

Pro Ala Lys Lys Val Thr Cys Cys Glu Pro Ile Ile Glu Pro Ala
1105                1110                1115                1120

Ser Pro Glu Pro Glu Thr Ala Glu Val Ser Ile Ala Asp Ile Glu Glu
                1125                1130                1135

Ala Phe Phe Glu Asp Pro Glu Glu Ile Pro Thr Ile Arg Leu Asn Met
            1140                1145                1150

Asp Ala Phe Thr Ser Asn Leu Lys Lys Ile Met Glu His Asn Lys Glu
        1155                1160                1165

Leu Gln Asp Gly Asn Met Ser Ser Ala Leu Val Ala Leu Thr Ala Glu
    1170                1175                1180

Thr Ala Ser Leu Pro Met Pro Lys Leu Lys Asn Ile Ser Gln Leu Arg
1185                1190                1195                1200

Thr Glu His Arg Val Tyr Glu Leu Pro Asp Glu His Pro Leu Leu Ala
                1205                1210                1215

Gln Leu Glu Lys Arg Glu Pro Asp Asp Pro Cys Ser Tyr Leu Leu Ala
            1220                1225                1230

Ile Trp Thr Pro Gly Glu Thr Ala Asp Ser Ile Gln Pro Ser Val Ser
        1235                1240                1245

Thr Cys Ile Phe Gln Ala Asn Gly Met Leu Cys Asp Glu Glu Thr Cys
    1250                1255                1260

Phe Ser Cys Asn Ser Ile Lys Glu Thr Arg Ser Gln Ile Val Arg Gly
1265                1270                1275                1280

Thr Ile Leu Ile Pro Cys Arg Thr Ala Met Arg Gly Ser Phe Pro Leu
                1285                1290                1295

Asn Gly Thr Tyr Phe Gln Val Asn Glu Val Phe Ala Asp His Ala Ser
            1300                1305                1310

Ser Leu Asn Pro Ile Asn Val Pro Arg Glu Leu Ile Trp Glu Leu Pro
        1315                1320                1325

Arg Arg Thr Val Tyr Phe Gly Thr Ser Val Pro Thr Ile Phe Lys Gly
    1330                1335                1340

Leu Ser Thr Glu Lys Ile Gln Ala Cys Phe Trp Lys Gly Tyr Val Cys
1345                1350                1355                1360

Val Arg Gly Phe Asp Arg Lys Thr Arg Gly Pro Lys Pro Leu Ile Ala
                1365                1370                1375

Arg Leu His Phe Pro Ala Ser Lys Leu Lys Gly Gln Gln Ala Asn Leu
            1380                1385                1390

Ala

<210> SEQ ID NO 7
<211> LENGTH: 1332
<212> TYPE: PRT
<213> ORGANISM: Arabidopsis thaliana
<220> FEATURE:
<223> OTHER INFORMATION: DML2 DNA glycosylase, demethylase

<400> SEQUENCE: 7

Met Glu Val Glu Gly Glu Val Arg Glu Lys Glu Ala Arg Val Lys Gly
  1               5                  10                  15
```

```
Arg Gln Pro Glu Thr Glu Val Leu His Gly Leu Pro Gln Glu Gln Ser
            20                  25                  30

Ile Phe Asn Asn Met Gln His Asn His Gln Pro Asp Ser Asp Arg Arg
        35                  40                  45

Arg Leu Ser Leu Glu Asn Leu Pro Gly Leu Tyr Asn Met Ser Cys Thr
    50                  55                  60

Gln Leu Leu Ala Leu Ala Asn Ala Thr Val Ala Thr Gly Ser Ser Ile
65                  70                  75                  80

Gly Ala Ser Ser Ser Leu Ser Ser Gln His Pro Thr Asp Ser Trp
                85                  90                  95

Ile Asn Ser Trp Lys Met Asp Ser Asn Pro Trp Thr Leu Ser Lys Met
            100                 105                 110

Gln Lys Gln Gln Tyr Asp Val Ser Thr Pro Gln Lys Phe Leu Cys Asp
        115                 120                 125

Leu Asn Leu Thr Pro Glu Glu Leu Val Ser Thr Ser Thr Gln Arg Thr
    130                 135                 140

Glu Pro Glu Ser Pro Gln Ile Thr Leu Lys Thr Pro Gly Lys Ser Leu
145                 150                 155                 160

Ser Glu Thr Asp His Glu Pro His Asp Arg Ile Lys Lys Ser Val Leu
                165                 170                 175

Gly Thr Gly Ser Pro Ala Ala Val Lys Lys Arg Lys Ile Ala Arg Asn
            180                 185                 190

Asp Glu Lys Ser Gln Leu Glu Thr Pro Thr Leu Lys Arg Lys Lys Ile
        195                 200                 205

Arg Pro Lys Val Val Arg Glu Gly Lys Thr Lys Lys Ala Ser Ser Lys
    210                 215                 220

Ala Gly Ile Lys Lys Ser Ser Ile Ala Ala Thr Ala Thr Lys Thr Ser
225                 230                 235                 240

Glu Glu Ser Asn Tyr Val Arg Pro Lys Arg Leu Thr Arg Arg Ser Ile
                245                 250                 255

Arg Phe Asp Phe Asp Leu Gln Glu Glu Asp Glu Glu Phe Cys Gly Ile
            260                 265                 270

Asp Phe Thr Ser Ala Gly His Val Glu Gly Ser Ser Gly Glu Glu Asn
        275                 280                 285

Leu Thr Asp Thr Thr Leu Gly Met Phe Gly His Val Pro Lys Gly Arg
    290                 295                 300

Arg Gly Gln Arg Arg Ser Asn Gly Phe Lys Lys Thr Asp Asn Asp Cys
305                 310                 315                 320

Leu Ser Ser Met Leu Ser Leu Val Asn Thr Gly Pro Gly Ser Phe Met
                325                 330                 335

Glu Ser Glu Glu Asp Arg Pro Ser Asp Ser Gln Ile Ser Leu Gly Arg
            340                 345                 350

Gln Arg Ser Ile Met Ala Thr Arg Pro Arg Asn Phe Arg Ser Leu Lys
        355                 360                 365

Lys Leu Leu Gln Arg Ile Ile Pro Ser Lys Arg Asp Arg Lys Gly Cys
    370                 375                 380

Lys Leu Pro Arg Gly Leu Pro Lys Leu Thr Val Ala Ser Lys Leu Gln
385                 390                 395                 400

Leu Lys Val Phe Arg Lys Lys Arg Ser Gln Arg Asn Arg Val Ala Ser
                405                 410                 415

Gln Phe Asn Ala Arg Ile Leu Asp Leu Gln Trp Arg Arg Gln Asn Pro
            420                 425                 430
```

```
Thr Gly Thr Ser Leu Ala Asp Ile Trp Glu Arg Ser Leu Thr Ile Asp
            435                 440                 445

Ala Ile Thr Lys Leu Phe Glu Glu Leu Asp Ile Asn Lys Glu Gly Leu
    450                 455                 460

Cys Leu Pro His Asn Arg Glu Thr Ala Leu Ile Leu Tyr Lys Lys Ser
465                 470                 475                 480

Tyr Glu Glu Gln Lys Ala Ile Val Lys Tyr Ser Lys Gln Lys Pro
                485                 490                 495

Lys Val Gln Leu Asp Pro Glu Thr Ser Arg Val Trp Lys Leu Leu Met
            500                 505                 510

Ser Ser Ile Asp Cys Asp Gly Val Asp Gly Ser Asp Glu Glu Lys Arg
            515                 520                 525

Lys Trp Trp Glu Glu Arg Asn Met Phe His Gly Arg Ala Asn Ser
            530                 535                 540

Phe Ile Ala Arg Met Arg Val Val Gln Gly Asn Arg Thr Phe Ser Pro
545                 550                 555                 560

Trp Lys Gly Ser Val Val Asp Ser Val Val Gly Val Phe Leu Thr Gln
                565                 570                 575

Asn Val Ala Asp His Ser Ser Ser Ala Tyr Met Asp Leu Ala Ala
            580                 585                 590

Glu Phe Pro Val Glu Trp Asn Phe Asn Lys Gly Ser Cys His Glu Glu
            595                 600                 605

Trp Gly Ser Ser Val Thr Gln Glu Thr Ile Leu Asn Leu Asp Pro Arg
    610                 615                 620

Thr Gly Val Ser Thr Pro Arg Ile Arg Asn Pro Thr Arg Val Ile Ile
625                 630                 635                 640

Glu Glu Ile Asp Asp Asp Glu Asn Asp Ile Asp Ala Val Cys Ser Gln
                645                 650                 655

Glu Ser Ser Lys Thr Ser Asp Ser Ser Ile Thr Ser Ala Asp Gln Ser
            660                 665                 670

Lys Thr Met Leu Leu Asp Pro Phe Asn Thr Val Leu Met Asn Glu Gln
            675                 680                 685

Val Asp Ser Gln Met Val Lys Gly Lys Gly His Ile Pro Tyr Thr Asp
690                 695                 700

Asp Leu Asn Asp Leu Ser Gln Gly Ile Ser Met Val Ser Ser Ala Ser
705                 710                 715                 720

Thr His Cys Glu Leu Asn Leu Asn Glu Val Pro Pro Glu Val Glu Leu
                725                 730                 735

Cys Ser His Gln Gln Asp Pro Glu Ser Thr Ile Gln Thr Gln Asp Gln
            740                 745                 750

Gln Glu Ser Thr Arg Thr Glu Asp Val Lys Lys Asn Arg Lys Lys Pro
            755                 760                 765

Thr Thr Ser Lys Pro Lys Lys Lys Ser Lys Glu Ser Ala Lys Ser Thr
    770                 775                 780

Gln Lys Lys Ser Val Asp Trp Asp Ser Leu Arg Lys Glu Ala Glu Ser
785                 790                 795                 800

Gly Gly Arg Lys Arg Glu Arg Thr Glu Arg Thr Met Asp Thr Val Asp
                805                 810                 815

Trp Asp Ala Leu Arg Cys Thr Asp Val His Lys Ile Ala Asn Ile Ile
            820                 825                 830

Ile Lys Arg Gly Met Asn Asn Met Leu Ala Glu Arg Ile Lys Ala Phe
            835                 840                 845
```

-continued

Leu Asn Arg Leu Val Lys Lys His Gly Ser Ile Asp Leu Glu Trp Leu
850                 855                 860

Arg Asp Val Pro Pro Asp Lys Ala Lys Glu Tyr Leu Leu Ser Ile Asn
865                 870                 875                 880

Gly Leu Gly Leu Lys Ser Val Glu Cys Val Arg Leu Leu Ser Leu His
                885                 890                 895

Gln Ile Ala Phe Pro Val Asp Thr Asn Val Gly Arg Ile Ala Val Arg
                900                 905                 910

Leu Gly Trp Val Pro Leu Gln Pro Leu Pro Asp Glu Leu Gln Met His
            915                 920                 925

Leu Leu Glu Leu Tyr Pro Val Leu Glu Ser Val Gln Lys Tyr Leu Trp
930                 935                 940

Pro Arg Leu Cys Lys Leu Asp Gln Lys Thr Leu Tyr Glu Leu His Tyr
945                 950                 955                 960

His Met Ile Thr Phe Gly Lys Val Phe Cys Thr Lys Val Lys Pro Asn
                965                 970                 975

Cys Asn Ala Cys Pro Met Lys Ala Glu Cys Arg His Tyr Ser Ser Ala
            980                 985                 990

Arg Ala Ser Ala Arg Leu Ala Leu Pro Glu Pro Glu Glu Ser Asp Arg
        995                 1000                1005

Thr Ser Val Met Ile His Glu Arg Ser Lys Arg Lys Pro Val Val
    1010                1015                1020

Val Asn Phe Arg Pro Ser Leu Phe Leu Tyr Gln Lys Glu Gln Glu
1025                1030                1035                1040

Ala Gln Arg Ser Gln Asn Cys Glu Pro Ile Ile Glu Glu Pro Ala Ser
                1045                1050                1055

Pro Glu Pro Glu Tyr Ile Glu His Asp Ile Glu Asp Tyr Pro Arg Asp
                1060                1065                1070

Lys Asn Asn Val Gly Thr Ser Glu Asp Pro Trp Glu Asn Lys Asp Val
            1075                1080                1085

Ile Pro Thr Ile Ile Leu Asn Lys Glu Ala Gly Thr Ser His Asp Leu
        1090                1095                1100

Val Val Asn Lys Glu Ala Gly Thr Ser His Asp Leu Val Val Leu Ser
1105                1110                1115                1120

Thr Tyr Ala Ala Ala Ile Pro Arg Arg Lys Leu Lys Ile Lys Glu Lys
                1125                1130                1135

Leu Arg Thr Glu His His Val Phe Glu Leu Pro Asp His His Ser Ile
                1140                1145                1150

Leu Glu Gly Phe Glu Arg Arg Glu Ala Glu Asp Ile Val Pro Tyr Leu
            1155                1160                1165

Leu Ala Ile Trp Thr Pro Gly Glu Thr Val Asn Ser Ile Gln Pro Pro
    1170                1175                1180

Lys Gln Arg Cys Ala Leu Phe Glu Ser Asn Asn Thr Leu Cys Asn Glu
1185                1190                1195                1200

Asn Lys Cys Phe Gln Cys Asn Lys Thr Arg Glu Glu Ser Gln Thr
            1205                1210                1215

Val Arg Gly Thr Ile Leu Ile Pro Cys Arg Thr Ala Met Arg Gly Gly
                1220                1225                1230

Phe Pro Leu Asn Gly Thr Tyr Phe Gln Thr Asn Glu Val Phe Ala Asp
            1235                1240                1245

His Asp Ser Ser Ile Asn Pro Ile Asp Val Pro Thr Glu Leu Ile Trp
1250                1255                1260

```
Asp Leu Lys Arg Arg Val Ala Tyr Leu Gly Ser Ser Val Ser Ser Ile
1265                1270                1275                1280

Cys Lys Gly Leu Ser Val Glu Ala Ile Lys Tyr Asn Phe Gln Glu Gly
            1285                1290                1295

Tyr Val Cys Val Arg Gly Phe Asp Arg Glu Asn Arg Lys Pro Lys Ser
            1300                1305                1310

Leu Val Lys Arg Leu His Cys Ser His Val Ala Ile Arg Thr Lys Glu
            1315                1320                1325

Lys Thr Glu Glu
    1330

<210> SEQ ID NO 8
<211> LENGTH: 1099
<212> TYPE: PRT
<213> ORGANISM: Arabidopsis thaliana
<220> FEATURE:
<223> OTHER INFORMATION: DML3 DNA glycosylase, demethylase

<400> SEQUENCE: 8

Met Glu Phe Ser Ile Asp Arg Asp Lys Asn Leu Leu Met Val Val Pro
 1               5                  10                  15

Glu Thr Arg Ile Lys Thr Lys Gln Phe Glu Lys Val Tyr Val Arg Arg
             20                  25                  30

Lys Ser Ile Lys Leu Pro Gln Asn Ser Met Val His Asn Thr Leu Ile
         35                  40                  45

Lys Met Ala Arg Gln Arg Ile Gln Lys Ser Met Lys Glu Ser Val Met
     50                  55                  60

Asn Gln His Ile Phe Lys Asn Phe Asp Ser Tyr Leu Ser Val Ile Tyr
 65                  70                  75                  80

His Pro Cys Cys Phe Val Ile Asn Asn Ser Gln Thr Thr His Lys Lys
                 85                  90                  95

Lys Glu Lys Lys Asn Ser Lys Glu Lys His Gly Ile Lys His Ser Glu
            100                 105                 110

Ser Glu His Leu Gln Asp Asp Ile Ser Gln Arg Val Thr Gly Lys Gly
        115                 120                 125

Arg Arg Arg Asn Ser Lys Gly Thr Pro Lys Lys Leu Arg Phe Asn Arg
    130                 135                 140

Pro Arg Ile Leu Glu Asp Gly Lys Lys Pro Arg Asn Pro Ala Thr Thr
145                 150                 155                 160

Arg Leu Arg Thr Ile Ser Asn Lys Arg Arg Lys Lys Asp Ile Asp Ser
                165                 170                 175

Glu Asp Glu Val Ile Pro Glu Leu Ala Thr Pro Thr Lys Glu Ser Phe
            180                 185                 190

Pro Lys Arg Arg Lys Asn Glu Lys Ile Lys Arg Ser Val Ala Arg Thr
        195                 200                 205

Leu Asn Phe Lys Gln Glu Ile Val Leu Ser Cys Leu Glu Phe Asp Lys
    210                 215                 220

Ile Cys Gly Pro Ile Phe Pro Arg Gly Lys Lys Arg Thr Thr Thr Arg
225                 230                 235                 240

Arg Arg Tyr Asp Phe Leu Cys Phe Leu Leu Pro Met Pro Val Trp Lys
                245                 250                 255

Lys Gln Ser Arg Arg Ser Lys Arg Arg Lys Asn Met Val Arg Trp Ala
            260                 265                 270

Arg Ile Ala Ser Ser Ser Lys Leu Leu Glu Glu Thr Leu Pro Leu Ile
        275                 280                 285
```

-continued

```
Val Ser His Pro Thr Ile Asn Gly Gln Ala Asp Ala Ser Leu His Ile
290                 295                 300
Asp Asp Thr Leu Val Arg His Val Val Ser Lys Gln Thr Lys Lys Ser
305                 310                 315                 320
Ala Asn Asn Val Ile Glu His Leu Asn Arg Gln Ile Thr Tyr Gln Lys
                325                 330                 335
Asp His Gly Leu Ser Ser Leu Ala Asp Val Pro Leu His Ile Glu Asp
            340                 345                 350
Thr Leu Ile Lys Ser Ala Ser Ser Val Leu Ser Glu Arg Pro Ile Lys
        355                 360                 365
Lys Thr Lys Asp Ile Ala Lys Leu Ile Lys Asp Met Gly Arg Leu Lys
370                 375                 380
Ile Asn Lys Lys Val Thr Thr Met Ile Lys Ala Asp Lys Lys Leu Val
385                 390                 395                 400
Thr Ala Lys Val Asn Leu Asp Pro Glu Thr Ile Lys Glu Trp Asp Val
                405                 410                 415
Leu Met Val Asn Asp Ser Pro Ser Arg Ser Tyr Asp Asp Lys Glu Thr
            420                 425                 430
Glu Ala Lys Trp Lys Lys Glu Arg Glu Ile Phe Gln Thr Arg Ile Asp
        435                 440                 445
Leu Phe Ile Asn Arg Met His Arg Leu Gln Gly Asn Arg Lys Phe Lys
450                 455                 460
Gln Trp Lys Gly Ser Val Val Asp Ser Val Val Gly Val Phe Leu Thr
465                 470                 475                 480
Gln Asn Thr Thr Asp Tyr Leu Ser Ser Asn Ala Phe Met Ser Val Ala
                485                 490                 495
Ala Lys Phe Pro Val Asp Ala Arg Glu Gly Leu Ser Tyr Tyr Ile Glu
            500                 505                 510
Glu Pro Gln Asp Ala Lys Ser Ser Glu Cys Ile Ile Leu Ser Asp Glu
        515                 520                 525
Ser Ile Ser Lys Val Glu Asp His Glu Asn Thr Ala Lys Arg Lys Asn
530                 535                 540
Glu Lys Thr Gly Ile Ile Glu Asp Glu Ile Val Asp Trp Asn Asn Leu
545                 550                 555                 560
Arg Arg Met Tyr Thr Lys Glu Gly Ser Arg Pro Glu Met His Met Asp
                565                 570                 575
Ser Val Asn Trp Ser Asp Val Arg Leu Ser Gly Gln Asn Val Leu Glu
            580                 585                 590
Thr Thr Ile Lys Lys Arg Gly Gln Phe Arg Ile Leu Ser Glu Arg Ile
        595                 600                 605
Leu Lys Phe Leu Asn Asp Glu Val Asn Gln Asn Gly Asn Ile Asp Leu
610                 615                 620
Glu Trp Leu Arg Asn Ala Pro Ser His Leu Val Lys Arg Tyr Leu Leu
625                 630                 635                 640
Glu Ile Glu Gly Ile Gly Leu Lys Ser Ala Glu Cys Val Arg Leu Leu
                645                 650                 655
Gly Leu Lys His His Ala Phe Pro Val Asp Thr Asn Val Gly Arg Ile
            660                 665                 670
Ala Val Arg Leu Gly Leu Val Pro Leu Glu Pro Leu Pro Asn Gly Val
        675                 680                 685
Gln Met His Gln Leu Phe Glu Tyr Pro Ser Met Asp Ser Ile Gln Lys
690                 695                 700
```

```
Tyr Leu Trp Pro Arg Leu Cys Lys Leu Pro Gln Glu Thr Leu Tyr Glu
705                 710                 715                 720

Leu His Tyr Gln Met Ile Thr Phe Gly Lys Val Phe Cys Thr Lys Thr
            725                 730                 735

Ile Pro Asn Cys Asn Ala Cys Pro Met Lys Ser Glu Cys Lys Tyr Phe
                740                 745                 750

Ala Ser Ala Tyr Val Ser Ser Lys Val Leu Leu Glu Ser Pro Glu Glu
            755                 760                 765

Lys Met His Glu Pro Asn Thr Phe Met Asn Ala His Ser Gln Asp Val
    770                 775                 780

Ala Val Asp Met Thr Ser Asn Ile Asn Leu Val Glu Glu Cys Val Ser
785                 790                 795                 800

Ser Gly Cys Ser Asp Gln Ala Ile Cys Tyr Lys Pro Leu Val Glu Phe
                805                 810                 815

Pro Ser Ser Pro Arg Ala Glu Ile Pro Glu Ser Thr Asp Ile Glu Asp
            820                 825                 830

Val Pro Phe Met Asn Leu Tyr Gln Ser Tyr Ala Ser Val Pro Lys Ile
        835                 840                 845

Asp Phe Asp Leu Asp Ala Leu Lys Lys Ser Val Glu Asp Ala Leu Val
850                 855                 860

Ile Ser Gly Arg Met Ser Ser Asp Glu Glu Ile Ser Lys Ala Leu
865                 870                 875                 880

Val Ile Pro Thr Pro Glu Asn Ala Cys Ile Pro Ile Lys Pro Pro Arg
                885                 890                 895

Lys Met Lys Tyr Tyr Asn Arg Leu Arg Thr Glu His Val Tyr Val
            900                 905                 910

Leu Pro Asp Asn His Glu Leu Leu His Asp Phe Glu Arg Arg Lys Leu
        915                 920                 925

Asp Asp Pro Ser Pro Tyr Leu Leu Ala Ile Trp Gln Pro Gly Glu Thr
    930                 935                 940

Ser Ser Ser Phe Val Pro Pro Lys Lys Cys Ser Ser Asp Gly Ser
945                 950                 955                 960

Lys Leu Cys Lys Ile Lys Asn Cys Ser Tyr Cys Trp Thr Ile Arg Glu
                965                 970                 975

Gln Asn Ser Asn Ile Phe Arg Gly Thr Ile Leu Ile Pro Cys Arg Thr
            980                 985                 990

Ala Met Arg Gly Ala Phe Pro Leu Asn Gly Thr Tyr Phe Gln Thr Asn
        995                 1000                1005

Glu Val Phe Ala Asp His Glu Thr Ser Leu Asn Pro Ile Val Phe Arg
    1010                1015                1020

Arg Glu Leu Cys Lys Gly Leu Glu Lys Arg Ala Leu Tyr Cys Gly Ser
1025                1030                1035                1040

Thr Val Thr Ser Ile Phe Lys Leu Leu Asp Thr Arg Arg Ile Glu Leu
                1045                1050                1055

Cys Phe Trp Thr Gly Phe Leu Cys Leu Arg Ala Phe Asp Arg Lys Gln
            1060                1065                1070

Arg Asp Pro Lys Glu Leu Val Arg Arg Leu His Thr Pro Pro Asp Glu
        1075                1080                1085

Arg Gly Pro Lys Phe Met Ser Asp Asp Ile
        1090                1095

<210> SEQ ID NO 9
<211> LENGTH: 48
<212> TYPE: DNA
<213> ORGANISM: Artificial Sequence
```

```
<220> FEATURE:
<223> OTHER INFORMATION: synthetic cloning primer JH151

<400> SEQUENCE: 9
tgaagagcca ttaccacttg atcctgcagg agggaatcga gcagctag                  48

<210> SEQ ID NO 10
<211> LENGTH: 48
<212> TYPE: DNA
<213> ORGANISM: Artificial Sequence
<220> FEATURE:
<223> OTHER INFORMATION: synthetic cloning primer JH152

<400> SEQUENCE: 10
agtggtaatg gctcttcagg aaacggtacc agccagtggg atagtctc                  48

<210> SEQ ID NO 11
<211> LENGTH: 22
<212> TYPE: DNA
<213> ORGANISM: Artificial Sequence
<220> FEATURE:
<223> OTHER INFORMATION: synthetic PCR amplification primer JH-RNseqF

<400> SEQUENCE: 11
cagatgtccg ctttctggta tg                                              22

<210> SEQ ID NO 12
<211> LENGTH: 19
<212> TYPE: DNA
<213> ORGANISM: Artificial Sequence
<220> FEATURE:
<223> OTHER INFORMATION: synthetic PCR amplification primer JH153

<400> SEQUENCE: 12
acagtgttcg ttgatcgag                                                  19

<210> SEQ ID NO 13
<211> LENGTH: 29
<212> TYPE: DNA
<213> ORGANISM: Artificial Sequence
<220> FEATURE:
<223> OTHER INFORMATION: synthetic PCR amplification primer JH154

<400> SEQUENCE: 13
ttaaggatcc tacaaaggag atggtgcac                                       29

<210> SEQ ID NO 14
<211> LENGTH: 36
<212> TYPE: DNA
<213> ORGANISM: Artificial Sequence
<220> FEATURE:
<223> OTHER INFORMATION: synthetic PCR amplification primer JH155

<400> SEQUENCE: 14
ttaagtcgac ttaggttttg ttgttcttca atttgc                               36

<210> SEQ ID NO 15
<211> LENGTH: 6
<212> TYPE: PRT
<213> ORGANISM: Artificial Sequence
<220> FEATURE:
<223> OTHER INFORMATION: synthetic 6xHis tag, poly-His

<400> SEQUENCE: 15

His His His His His His
 1               5
```

US 8,951,769 B2

ENGINEERED DEMETER 5-METHYLCYTOSINE DNA GLYOSYLASE WITH IMPROVED YIELD, STABILITY AND SOLUBILITY

CROSS REFERENCE TO RELATED PATENT APPLICATIONS

The present application is the US National Phase entry under 35 U.S.C. §371 and claims the benefit of International Application No. PCT/US2010/031623, filed Apr. 19, 2010, which claims the benefit of U.S. Provisional Patent Application No. 61/170,978, filed Apr. 20, 2009, which are incorporated by reference for all purposes.

STATEMENT AS TO RIGHTS TO INVENTIONS MADE UNDER FEDERALLY SPONSORED RESEARCH AND DEVELOPMENT

The invention was made with government support under Grant Number R01 GM069415 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -1985-1.TXT, created on Feb. 10, 2012, 61,440 bytes, machine format IBM-PC, MS-Windows operating system, is hereby incorporated by reference in its entirety for all purposes.

BACKGROUND OF THE INVENTION

Alleles of imprinted genes are expressed differently depending on whether they are inherited from the male or female parent. Imprinting regulates a number of genes essential for normal development in mammals and angiosperms. In mammals, imprinted genes contribute to the control of fetal growth and placental development (Constancia, M. et al., *Nature*, 432, 53-57 (2004)). Human diseases are linked to mutations in imprinted genes or aberrant regulation of their expression (Constancia, M. et al., *Nature*, 432, 53-57 (2004)). Mechanisms of distinguishing maternal and paternal alleles have been extensively characterized in mammals. Imprinted genes reside in chromosomal clusters and are regulated by differentially methylated imprinting control regions (ICRs) (Reik, W. and Walter, J., *Nat Rev Genet*, 2, 21-32 (2001)). Differential DNA methylation is established during oogenesis or spermatogenesis by de novo methyltransferases and maintained somatically by the CG maintenance methyltransferase Dnmt1 (Li, E. (2002). *Nat Rev Genet*. 3, 662-673. ICRs are subject to differential histone modifications and in some instances can act as chromatin boundaries (Delaval, K. and Feil, R., *Curr Opin Genet Dev.*, 14, 188-195 (2004)). Other mechanisms to regulate allele-specific gene expression involve non-coding RNAs, including antisense transcripts and microRNAs (O'Neill, 2005). Polycomb group (PcG) proteins, which function in large complexes to methylate histones and modify chromatin (Cao, R. and Zang, Y., *Curr Opin Genet Dev.*, 14, 155-164 (2004)), maintain allele-specific silencing of some imprinted genes (Delaval, K. and Feil, R., *Curr Opin Genet Dev.*, 14, 188-195 (2004)).

The endosperm, one of the products of angiosperm double fertilization, is an important site of imprinting in plants (Gehring, M. et al., *Plant Cell*, 16, S203-S213 (2004)) and has functions analogous to the placenta. In flowering plants, meiosis followed by mitosis produces the female and male gametophytes. Two cells of the female gametophyte, the haploid egg and the diploid central cell, are fertilized by two haploid sperm from the male gametophyte to form the diploid embryo and triploid endosperm, respectively. The endosperm provides nutrients to the embryo during seed development and, in *Arabidopsis*, is almost entirely consumed by the time embryo maturation is completed.

Molecular events that take place in the female gametophyte before fertilization have an essential role in endosperm gene imprinting. The imprinting of two genes, MEA and FWA, is regulated by DEMETER (DME, also sometime abbreviated DMT), a helix-hairpin-helix DNA glycosylase (Choi, Y. et al., *Cell*, 110, 33-42 (2002); Kinoshita, T. et al., *Science*, 303, 521-523 (2004)). DME has also been referred to in the literature as Atropos (ATR). The DME plant gene product has been described to control plant phenotypes and affect DNA methylation. The DME gene product is described in, e.g., U.S. Pat. Nos. 6,476,296 and 7,109,394 as well as Choi, Y. et al., *Cell*, 110:33-42 (2002); Gehring, M. et al., *Cell*, 124:495-506 (2006).

DNA glycosylases function in the base excision repair pathway by removing damaged or mismatched bases from DNA (Scharer, O. D. and Jiricny, J., *BioEssays*, 23, 270-281 (2001)). Bifunctional helix-hairpin-helix DNA glycosylases have both DNA glycosylase and apurinic/apyrimidinic (AP) lyase activities. The DNA glycosylase activity removes the damaged or mispaired base by cleaving the N-glycosylic bond, creating an abasic site, whereas the lyase activity nicks the DNA. An AP endonuclease generates a 3'-hydroxyl used by a DNA repair polymerase that inserts the proper nucleotide. A DNA ligase seals the nick to complete the repair process. DNA glycosylase/lyases have not been implicated in mammalian imprinting mechanisms.

Both MEA and FWA are expressed in the central cell before fertilization and in the endosperm, from the maternal allele, after fertilization (Kinoshita, T. et al., *Science*, 303, 521-523 (2004); Kinoshita, T. et al., *Plant Cell*, 11, 1945-1952 (2004); Vielle-Calzada, J. P. et al., *Genes Dev*, 13, 2971-2982 (1999)). In contrast, DME is expressed in the central cell of the female gametophyte but not in the endosperm (Choi, Y. et al., *Cell*, 110, 33-42 (2002)). Expression of MEA and FWA in the central cell and early endosperm is dependent on DME (Choi, Y. et al., *Cell*, 110, 33-42 (2002); Kinoshita, T. et al., *Science*, 303, 521-523 (2004)).

Though maternal expression of MEA and FWA is controlled by DME, there are important distinctions regarding the regulation of expression of these genes. FWA is silent in all vegetative and reproductive tissues except for expression of the maternal allele in the female gametophyte and endosperm (Kinoshita, T. et al., *Science*, 303, 521-523 (2004); Soppe, W. J. J. et al., *Mol Cell*, 6, 791-802 (2000)). MEA is imprinted in the endosperm, but is biallelically expressed in the embryo and in other sporophytic tissues (Kinoshita, T. et al., *Science*, 303, 521-523 (2004)). Expression of MEA in the embryo is likely not under DME control, as DME expression is not detected in the egg cell or embryo (Choi, Y. et al., *Cell*, 110, 33-42 (2002)). Expression of FWA in the endosperm, and elsewhere in the plant, is associated with hypomethylation of repeats in the 5' region of the gene (Kinoshita, T. et al., *Science*, 303, 521-523 (2004); Soppe, W. J. J. et al., *Mol Cell*, 6, 791-802 (2000)). Paternal inheritance of met1 releases FWA paternal allele silencing in the endosperm and embryo (Kinoshita, T. et al., *Science*, 303, 521-523 (2004)). MET1 is the homolog of Dnmt1 (Bender, J., *Ann Rev Plant Biology,* 55, 41-68 (2004)).

DME, MEA, and MET1 genetically interact in the female gametophyte. MEA is an E(z) homologue that functions in a PcG complex along with FIE (Kohler, C. et al., *EMBO J,* 22, 4804-4814 (2003)), a homologue of Eed, to repress endosperm growth. Inheritance of mutant maternal dme or mea alleles causes endosperm overproliferation, embryo arrest, and seed abortion (Choi, Y. et al., Cell, 110, 33-42 (2002); Grossniklaus, U. et al., *Science,* 280, 446-450 (1998); Kiyosue, T. et al., *Proc Natl Acad Sci USA,* 96, 4186-4191 (1999); Luo, M. et al., *Proc Natl Acad Sci USA,* 96, 296-301 (1999)). Seed abortion caused by dme is suppressed by maternally inherited met1 if a wild type maternal MEA allele is present (Xiao, W. et al., *Developmental Cell,* 5, 891-901 (2003)). Moreover, met1 can restore MEA expression in dme mutants (Xiao, W. et al., *Developmental Cell,* 5, 891-901 (2003)). It is known that the glycosylase activity of DME is necessary for seed viability and activation of MEA transcription (Choi, Y. et al., *Proc Natl Acad Sci USA,* 101, 7481-7486 (2004)). DME antagonizes MET1 by specifically removing 5'-methylcytosine from MEA in the central cell, allowing the maternal MEA allele to be expressed there before fertilization and in the endosperm after fertilization.

As mentioned above, genetic information is stored not only in the sequential arrangement of four nucleotide bases, but also in covalent modification of selected bases (see, e.g., Robertson et al., Nature Rev. Genet. 1:11-19 (2000)). One of these covalent modifications is methylation of cytosine nucleotides, particularly cytosines adjacent to guanine nucleotides in "CpG" dinucleotides. Covalent addition of methyl groups to cytosine within CpG dinucleotides is catalyzed by proteins from the DNA methyltransferase (DNMT) family (Amir et al., Nature Genet. 23:185-88 (1999); Okano et al., Cell 99:247-57 (1999)). In the human genome, CpG dinucleotides are generally under represented, and many of the CpG dinucleotides occur in distinct areas called CpG islands. A large proportion of these CpG islands can be found in promoter regions of genes. The conversion of cytosine to 5'-methylcytosine in promoter associated CpG islands has been linked to changes in chromatin structure and often results in transcriptional silencing of the associated gene. Transcriptional silencing by DNA methylation has been linked to mammalian development, imprinting and X-Chromosome inactivation, suppression of parasitic DNA and numerous cancer types (see, e.g., Li et al., Cell 69:915-26 (1992); Okano et al., Cell 99:247-57 (1999)). Detected changes in the methylation status of DNA can serve as markers in the early detection of neoplastic events (Costello et al., Nature Genet. 24:132-38 (2000)).

BRIEF SUMMARY OF THE INVENTION

The present invention provides, in part, a isolated cell comprising a heterologous expression cassette, the expression cassette comprising a promoter operably linked to a polynucleotide, the polynucleotide encoding a polypeptide comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids and wherein the polypeptide excises methylated cytosines in DNA when contacted to DNA comprising methylated cytosines.

In some embodiments, the first and second amino acid sequences are linked directly.

In some embodiments, the first and second amino acid sequences are linked indirectly via the amino acid linker In some embodiments, the linker is heterologous to the first or second amino acid sequence. In some embodiments, the linker is comprises a fragment of at least 10 amino acids of SEQ ID NO:3 but does not include the full sequence of SEQ ID NO:3. In some embodiments, the linker has 20 or fewer amino acids. In some embodiments, the linker comprises SEQ ID NO:4.

In some embodiments, the first amino acid sequence is at least 95% identical to SEQ ID NO:1. In some embodiments, the second amino acid sequence is at least 95% identical to SEQ ID NO:2. In some embodiments, the first amino acid sequence comprises SEQ ID NO:1 and the second amino acid sequence comprises SEQ ID NO:2.

In some embodiments, the cell is a eukaryotic cell. In some embodiments, the cell is a yeast, fungal, mammalian, plant or insect cell.

In some embodiments, the cell is a prokaryotic cell.

The present invention also provides methods of making a polypeptide that excises methylated cytosines in DNA when contacted to DNA comprising methylated cytosines. In some embodiments, the method comprises culturing the cell as described above or elsewhere herein under conditions to allow for expression of the polypeptide.

In some embodiments, the method further comprises purifying the polypeptide.

In some embodiments, the first and second amino acid sequences are linked directly.

In some embodiments, the first and second amino acid sequences are linked indirectly via the amino acid linker. In some embodiments, the linker is heterologous to the first or second amino acid sequence. In some embodiments, the linker is comprises a fragment of at least 10 amino acids of SEQ ID NO:3 but does not include the full sequence of SEQ ID NO:3. In some embodiments, the linker has 20 or fewer amino acids. In some embodiments, the linker comprises SEQ ID NO:4.

In some embodiments, the first amino acid sequence is at least 95% identical to SEQ ID NO:1. In some embodiments, the second amino acid sequence is at least 95% identical to SEQ ID NO:2. In some embodiments, the first amino acid sequence comprises SEQ ID NO:1 and the second amino acid sequence comprises SEQ ID NO:2.

In some embodiments, the cell is a eukaryotic cell. In some embodiments, the cell is a yeast, fungal, mammalian or insect cell.

In some embodiments, the cell is a prokaryotic cell.

The present invention also provides isolated polypeptides comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids and wherein the polypeptide excises methylated cytosines in DNA when contacted to DNA comprising methylated cytosines. In some embodiments, the polypeptides are produced by the methods described above.

In some embodiments, the first and second amino acid sequences are linked directly.

In some embodiments, the first and second amino acid sequences are linked indirectly via the amino acid linker. In some embodiments, the linker is heterologous to the first or second amino acid sequence. In some embodiments, the linker is comprises a fragment of at least 10 amino acids of SEQ ID NO:3 but does not include the full sequence of SEQ ID NO:3. In some embodiments, the linker has 20 or fewer amino acids. In some embodiments, the linker comprises SEQ ID NO:4.

In some embodiments, the first amino acid sequence is at least 95% identical to SEQ ID NO:1. In some embodiments, the second amino acid sequence is at least 95% identical to SEQ ID NO:2. In some embodiments, the first amino acid sequence comprises SEQ ID NO:1 and the second amino acid sequence comprises SEQ ID NO:2.

The present invention also provides an isolated nucleic acid comprising an expression cassette, the expression cassette comprising a promoter operably linked to a polynucleotide encoding a polypeptide, the polynucleotide encoding a polypeptide comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids and wherein the polypeptide excises methylated cytosines in DNA when contacted to DNA comprising methylated cytosines.

In some embodiments, the first and second amino acid sequences are linked directly.

In some embodiments, the first and second amino acid sequences are linked indirectly via the amino acid linker. In some embodiments, the linker is heterologous to the first or second amino acid sequence. In some embodiments, the linker is comprises a fragment of at least 10 amino acids of SEQ ID NO:3 but does not include the full sequence of SEQ ID NO:3. In some embodiments, the linker has 20 or fewer amino acids. In some embodiments, the linker comprises SEQ ID NO:4.

In some embodiments, the first amino acid sequence is at least 95% identical to SEQ ID NO:1. In some embodiments, the second amino acid sequence is at least 95% identical to SEQ ID NO:2. In some embodiments, the first amino acid sequence comprises SEQ ID NO:1 and the second amino acid sequence comprises SEQ ID NO:2.

The present invention also provides methods of detecting cytosine methylation in a DNA sample. In some embodiments, the method comprises contacting DNA with a polypeptide as described herein (e.g., comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids) such that the polypeptide excises methylated cytosines, if present, from the DNA, thereby cleaving the DNA strand having the methylated cytosine to cause a nick in the DNA; extending a primer that is complementary to a sequence in the DNA up to the nick, thereby producing an extension product; and detecting the extension product, wherein the quantity or length of the extension product indicates cytosine methylation in the DNA sample, wherein the method does not involve adding nucleotides to the extension product with a terminal transferase.

The present invention also provides methods of detecting DNA methylation in a DNA sample. In some embodiments, the method comprises contacting DNA with the polypeptide as described herein (e.g., comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids) under conditions such that the demethylase excises methylated cytosines, if present, from the DNA, thereby cleaving the DNA strand having the methylated cytosine to cause a nick in the DNA; extending a detectably-labeled primer that is complementary to a sequence in the DNA up to the nick, thereby producing an extension product; and detecting the length of the extension product, thereby detecting methylation of the DNA in the DNA sample.

The present invention also provides methods of detecting DNA methylation in a DNA sample. In some embodiments, the method comprises contacting DNA with the polypeptide as described herein (e.g., comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids) under conditions such that the polypeptide becomes covalently linked to the DNA at the site of methylated cytosines, if present, thereby cleaving the DNA strand having the methylated cytosine to cause a nick in the DNA; separating double stranded DNA covalently bound to the polypeptide from DNA not bound to the polypeptide, wherein the double stranded DNA covalently bound to the polypeptide comprises a first strand covalently linked to the polypeptide and a complementary strand not linked to the polypeptide; and amplifying DNA on the complementary strand and detecting an amplification product, thereby detecting DNA methylation in a DNA sample.

The present invention also provides methods of detecting DNA methylation in a DNA sample. In some embodiments, the method comprises contacting DNA with the polypeptide as described herein (e.g., comprising a first amino acid sequence substantially identical to SEQ ID NO:1 linked to a second amino acid sequence substantially identical to SEQ ID NO:1, wherein the first and second amino acid sequences are linked directly or by a linker having between 1-300 amino acids) under conditions such that the polypeptide excises methylated cytosines, if present, from the DNA, thereby cleaving the DNA strand having the methylated cytosine to cause a nick in the DNA; amplifying a region of DNA between two primers that are complementary to chromosomal DNA; and detecting the quantity of an amplification product, wherein the presence, absence and/or quantity of the amplification product is indicative of methylation of the DNA in the DNA sample.

DEFINITIONS

The term "a" refers to at least one of something.

"Cytosine methylation" refers to 5-methyl cytosine.

"Methylated DNA" refers to DNA comprising 5-methyl cytosine.

The term "nucleic acid" or "polynucleotide" as used herein refers to a deoxyribonucleotide or ribonucleotide in either single- or double-stranded form. The term encompasses nucleic acids containing analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189-197. Other synthetic backbones encompassed by the term include methyl-phosphonate linkages or alternating methylphosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156).

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds, embryos, endosperm, ovules, male and female gametophytes, and plant cells and progeny of same. The class of plants which can be used in the method of the invention is generally as broad as the class of flowering plants amenable to transformation techniques, including angiosperms (monocotyledonous and dicotyledonous plants), as well as gymnosperms. It includes plants and plant cells of a variety of ploidy levels, including polyploid, diploid, haploid, aneuploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like. "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a T0 for the primary transgenic plant and T1 for the first generation. The term "exogenous" as used herein is also intended to encompass inserting a naturally found element into a non-naturally found location.

The phrase "host cell" refers to a cell from any organism. Exemplary host cells are derived from plants, bacteria, yeast, fungi, insects or animals, including humans. Methods for introducing polynucleotide sequences into various types of host cells are well known in the art. Host cells can be isolated from an organism rather than as part of an organism.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

"Demethylase activity" refers to the ability of a polypeptide to excise a methylated nucleotide (e.g., 5-methyl cytosine) from a DNA sequence. Demethylation activity can be assayed in vivo by expressing a candidate polypeptide in the nucleus of a cell and then assaying for a change in methylation of the cell's DNA. See, e.g., Vong, et al., *Science* 260:1926-1928 (1993). Changes in chromosomal methylation can be measured by comparing the ability of methylation sensitive and insensitive endonucleases to cleave DNA from a cell expressing a polypeptide suspected of having demethylase or methylase activity. Alternatively, bisulfate sequencing can be used to identify which base pairs are methylated in a DNA sequence. For a discussion of both methods, see Soppe, W. J. J. et al., *Mol Cell,* 6, 791-802 (2000). In vitro assays to measure demethylase activity using labeled substrates are also known to those of skill in the art. See, e.g., Vhu et al., *Proc. Natl. Acad. Sci. USA* 97:5135-5139 (2000). Further methods for measuring demethylase activity are provided in the Examples.

The phrase "substantially identical," in the context of two nucleic acids or polypeptides, refers to a sequence or subsequence that has at least 40% sequence identity with a reference sequence. Alternatively, percent identity can be any integer from 40% to 100%. Exemplary embodiments include at least: 40%, 45%, 50%, 55%, 60%, 65%, 70%, 75%, 80%, 85%, 90%, 95%, or 99% compared to a reference sequence using the programs described herein; preferably BLAST using standard parameters, as described below. As explained herein, the present invention provides sequences substantially identical to SEQ ID NOs:1, 2, 3, and 4, and notably polypeptides (and nucleic acids encoding such polypeptides) comprising amino acid sequences substantially identical to SEQ ID NO:1 and SEQ ID NO:2 linked directly or via a linker.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. If no range is provided, the comparison window is the entire length of the reference sequence. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

An example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 55° C., sometimes 60° C., and sometimes 65° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946, 778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

BRIEF DESCRIPTION OF THE DRAWINGS

FIG. 2 displays a schematic drawing of (DMEΔ677ΔIDR1::lnk), which comprises the Δ677 deletion further lacking the IDR1 region (DMEΔ677ΔIDR1::lnk) (left) (AGSSGNGSSGNG=SEQ ID NO:4). Also shown are results of an in vitro assay demonstrating that DMEΔ677ΔIDR1::lnk enzyme is active and has lyase activity on a double stranded DNA substrate with a single 5-methylcytosine residue.

FIG. 3 displays expression of DMEΔ677ΔIDR1::lnk fused to various protein fusion partners.

FIG. 4 displays results of various steps of purification of poly-His tagged (DMEΔ677ΔIDR1::lnk).

FIG. 5 displays selected results for DME full length, Δ667 and (DMEΔ677ΔIDR1::lnk).

DEMETER (DME) is a DNA glycosylase that excises 5-methylcytosine from DNA leading to active DNA demethylation. DME uniquely excises 5-methylcytosine in all sequence contexts. However, production of DME (full length and DMEΔN677) in *E. coli* is difficult because of its large size (1,729 amino acids) and poor solubility. As shown in FIG. 1, in this invention, we engineered DME by removing interdomain region 1 (IDR1) and replacing it with a small linker (lnk). The size of DMEΔN677ΔIDR1::lnk is only 38.9% of full-length DME, and its expression level in *E. coli* significantly increased. This improved both yield and solubility while preserving enzyme activity (FIG. 2). When fused with different types of tags (e.g., 6×His (SEQ ID NO:15), maltose-binding protein, small ubiquitin-like modifier, glutathione S transferase, and thioredoxin) and produced in *E. coli*, DMEΔN677ΔIDR1::lnk was successfully expressed and highly soluble in all cases (FIG. 3). His-tagged DMEΔN677ΔIDR1::lnk was successively purified over Nickel, Heparin, and Superdex 200 columns with improved stability and little degradation and/or truncation (FIG. 4). FIG. 5 summarizes the properties of DME, DMEΔN677, and DMEΔN677ΔIDR1::lnk.

DETAILED DESCRIPTION

I. Introduction

Figure 1:
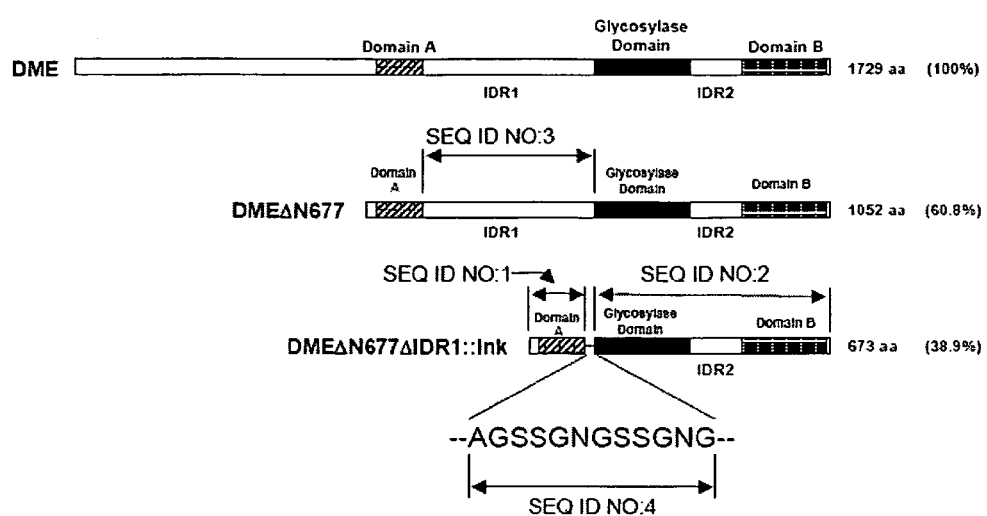
FIG. 1 displays a schematic drawing of the full length *Arabidopsis* DME polypeptide (top), the Δ677 N-terminus DME deletion (middle) and the Δ677 deletion further lacking the IDR1 region (bottom). The deleted IDR1 sequence is SEQ ID NO:3. In its place, a linker (SEQ ID NO:4) was inserted.

The present invention is based, in part, on the discovery that it is possible to delete all or part of an internal portion (referred to herein as "IDR1") of the DEMETER amino acid sequence while maintaining protein activity. Further, the inventors have found that the internally truncated protein has substantially better expression (yield) when expressed from *E. coli*. It is expected that a similar improvement of expression will occur when using other prokaryotic or eukaryotic expression systems.

II. Demethylases

The present invention provides for novel DME polypeptides with internal deletions that retain demethylase activity. It was previously known that that as many as 677 amino acids can be deleted from the amino terminus of DME while retaining demethylase activity. See, e.g., U.S. patent application Ser. No. 12/006,779. The inventors have now found that a further internal portion of DME can be deleted while maintaining activity of the protein and greatly improving solubility and expression and yield when produced in cells. Accordingly, the present invention provides for polypeptide that excise methylated cytosines in DNA when contacted to DNA comprising methylated cytosines, wherein the polypeptides comprise a first amino acid sequence substantially (e.g., at least 70%, 80%, 90%, 95%) identical to SEQ ID NO:1 linked directly or linked through a linker to a second amino acid sequence substantially (e.g., at least 70%, 80%, 90%, 95%) identical to SEQ ID NO:2. The inventors have found, for example, that a heterologous linker (i.e., not a sequence or fragment thereof from SEQ ID NO:3, the IDR1 sequence) can be used to link the first and second amino acid sequences together (where the first amino acid sequence is nearer to the N-terminus of the protein than the second amino acid sequence).

A variety of linkers can be used to link the first and second amino acid sequences. In some embodiments, the first and second sequences are linked directly. In some embodiments, a linker links the first and second amino acid sequences. In some embodiments, the linker is a fragment, but not the entire sequence, of SEQ ID NO:3. For example, the linker can be a fragment of at least 2, 5, 10, 20, 50 or more amino acids of SEQ ID NO:3. In some embodiments, the fragment of SEQ ID NO:3 has fewer than 100, 50, 30, 20, or 10 amino acids.

Alternatively, a heterologous linker can be used. A wide variety of amino acid linkers are known and can be used. In some embodiments, the heterologous linker has between 2-30 amino acids, e.g., 5-25 amino acids. In some embodiments, at least a majority of the amino acids in the heterologous linker are serine, alanine or arginine. An exemplary heterologous linker is SEQ ID NO:4.

The present invention further provides numerous chimeric polypeptides with demethylase activity, the chimeric polypeptides comprising the fusion of portions of at least two different demethylases (i.e., a sequence corresponding (substantially identical) to SEQ ID NO:1 from one protein and a sequence corresponding (substantially identical) to SEQ ID NO:2 of a second enzyme) but lacking a sequence corresponding to IDR1 (e.g., lacking a sequence substantially identical to SEQ ID NO:3). Exemplary demethylases from which chimeras can be constructed include, e.g., DME (SEQ ID NO:5), ROS1 (SEQ ID NO:6), DML2 (SEQ ID NO:7), or DML3 (SEQ ID NO:8).

Optionally, the demethylases of the invention are fused with a further polypeptide sequence that can be used, e.g., to assist in purification of the demethylase and/or assist in rendering the demethylases more soluble. Examples of further polypeptides to which the demethylases can be fused include, e.g., maltose binding protein (MBP), glutathione (GST), poly-His, etc.

The present invention also provides polynucleotides encoding any of the demethylase polypeptides described herein. In some embodiments, the polynucleotides of the invention comprise an expression cassette, the expression cassette comprising a promoter operably linked to a polynucleotide encoding a demethylase described herein. The promoter can be a promoter that initiates and/or controls transcription in prokaryotic and/or eukaryotic cells. The promoter can initiate and/or control transcription in plant, animal, insect or other eukaryotic cells.

One of skill will appreciate that the polypeptides of the invention can be produced by standard recombinant genetic engineering methods. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). For example, an expression cassette encoding the polypeptide can be introduced into a cell. In some embodiments, a single or multi-copy expression vector comprising the expression cassette is introduced into the cell. A wide variety of prokaryotic and eukaryotic expression systems can be used.

In some embodiments, to obtain high level expression of a polypeptide, one subclones polynucleotides encoding a polypeptide of the invention into an expression vector that contains a strong promoter to direct transcription, a transcription/translation terminator, and a ribosome binding site for translational initiation. Suitable bacterial promoters are well known in the art and described, e.g., in Sambrook et al. and Ausubel et al. Bacterial expression systems for expressing the polypeptides of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with an polypeptides of the invention-encoding sequence under the direction of the polyhedrin promoter or other strong baculovirus promoters.

Standard transfection methods are used to produce bacterial, mammalian, yeast or insect cell lines that express large quantities of polypeptides of the invention, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra).

As desired, after the expression vector is introduced into the cells, the transfected cells are cultured under conditions favoring expression of polypeptides of the invention, which is recovered from the culture using standard techniques identified below.

III. Detection of Methylation

As the demethylases of the invention bind to methylated DNA sequences and modify such sequences, demethylases are useful for detecting the presence or absence and/or the location (i.e., specific sequence) of cytosine methylation in DNA. Cytosine methylation is known to regulate transcription, thereby affecting biological processes in cells and organisms. Accordingly, detection of DNA methylation has numerous uses in biological research. Moreover, aberrant methylation can be a marker for aging and disease, including various cancers. See, e.g., Jones, *Oncogene,* 21(35):5358-5360 (2002); Esteller, *Annual Review of Pharmacology and Toxicology,* 45: 629-656 (2005); Li, *Biochim Biophys Acta.,* 21704(2):87-102 (2004); Szyf, *Biochem Pharmacol.,* 68(6): 1187-97 (2004). Exemplary human genes whose methylation status is implicated in cancer and/or aging and can be detected according to the methods of the present invention include, but are not limited to, e.g., 14-3-3 Sigma, ABL1 (P1), ABO, APC, AR (Androgen Receptor), BLT1 (Leukotriene B4 Receptor), BRCA1, CALCA (Calcitonin), CASP8 (CASPASE 8), Caveolin 1, CD44, CFTR, COX2, CSPG2 (Versican), CX26 (Connexin 26), Cyclin A1, DBCCR1, ECAD (E-cadherin), Endothelin Receptor B, EPHA3, EPO (Erythropoietin), ER (Estrogen Receptor), FHIT, GPC3 (Glypican 3), GST-pi, H19, H-Cadherin (CDH13), HIC1, hMLH1, HOXA5, IGF2 (Insulin-Like Growth Factor II), IGFBP7, IRF7, LKB1, LRP-2 (Megalin), MDGI (Mammary-derived growth inhibitor), MDR1, MDR3 (PGY3), MGMT (O6 methyl guanine methyl transferase), MT1a (metallothionein 1), MUC2, MYOD1, N33, NEP (Neutral Endopeptidase 24.1)/CALLA, NF-L (light-neurofilament-encoding gene), NIS (sodium-iodide symporter gene), p14/ARF, p15 (CDKN2B), p16 (CDKN2A), p27KIP1, p57 KIP2, PAX6, PgR (Progesterone Receptor), RAR-Beta2, RASSF1, RB1 (Retinoblastoma), TERT, TESTIN, TGFBRI, THBS1 (Thrombospondin-1), TIMP3, TLS3 (T-Plastin), Urokinase (uPA), VHL (Von-Hippell Lindau), WT1, ZO2 (Zona Occludens 2). Accordingly, the present invention provides for detecting methylation of these or other mammalian (e.g., human) gene sequences, including, e.g., promoters thereof), by any methylation detection method provided herein. The DNA samples can be obtained from any mammal, including humans, and can be any biological sample that contains DNA, include, but not limited to, tissue biopsies (e.g., solid tumors or tissues suspect of having cancer or pre-cancerous tissue), blood samples, stool samples, etc.

The DNA methylation detection methods of the present invention can be used to detect DNA methylation, including for use in determining a diagnosis or prognosis, or, e.g., for monitoring progress of a disease or drug therapy.

Demethylases useful for the DNA methylation detection methods described herein include any demethylase that causes a nick when excising a methylated cytosine.

A. Methods Involving Primer Extension

Numerous methods of DNA methylation detection are provided herein. In some embodiments, the methods take advantage of the DNA "nicking" activity of the polypeptides of the present invention. "Nicking" refers to an activity of demethylases in which at least one strand of the DNA double helix is cleaved at or adjacent to a methylated nucleotide (e.g., a methylated cytosine) on the phosphodiester backbone of the DNA. See, e.g., Gehring, M. et al., *Cell,* 124:495-506 (2006).

In some embodiments, the methods comprise nicking DNA with a demethylase of the invention and using primer extension from a DNA sequence adjacent to a DNA region of interest to detect the nick and thus the methylated nucleotide. In these embodiments, the primer extension continues until it is stopped by the nick. Determination of the length of the extension product, with knowledge of the chromosomal sequence and the sequence to which the primer hybridizes on the chromosomal sequence, allows one to determine where the methylation occurs in the chromosome. For example, if the extension product is 100 nucleotides long, then the methylated nucleotide is approximately 100 nucleotides from the site to which the primer hybridizes. Determination of the quantity of the primer extension product is indicative of the amount of methylated DNA. For example, if only 50% of the chromosomal copies are methylated (or if 50% of the cells in a sample from which DNA is obtain have methylated copies) then there will be a long extension product at the limits of primer extension and a shorter extension product which results from the nick stopping the extension, each in approximately equal amounts. In some embodiments, multiple different length extension products of different quantity are detected, thereby detecting a complicated heterogeneous methylation pattern of a sample, thereby detecting methylation at multiple sites on the DNA.

Primer extension can be performed by any method that allow for polymerase-based extension of a primer hybridized to genomic DNA. In some embodiments, simple primer extension involves addition of a primer and DNA polymerase to genomic DNA under conditions to allow for primer hybridization and primer extension by the polymerase. Of course, such a reaction includes the necessary nucleotides, buffers, and other reagents known in the art for primer extension.

In some embodiments, primer extension occurs during a nucleic acid amplification reaction. A non-limiting example of nucleic acid amplification is the polymerase chain reaction (PCR). Additional examples of amplification reactions include the ligase chain reaction (LCR), strand displacement amplification (SDA) (Walker, et al. *Nucleic Acids Res.* 20(7): 1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313): 91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell. Probes* 13(4):315-320 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS. In embodiments involving amplification, one or more primers are extended by amplification following nicking of the genomic DNA template with a demethylase of the invention, and the amplification product quantity or length is determined. Any number of methods are known for detecting amplification products, including, e.g., real-time amplification techniques, including those involving probes that specifically detect amplification products in real time, such as TaqMan® probes, Molecular Beacons and the like.

In some embodiments, the primer is detectably labeled (e.g., at its 5' end or otherwise located to not interfere with 3' extension of the primer) and following primer extension, the length and/or quantity of the labeled extension product is detected by detecting the label.

In some embodiments, the primer extension products are detected by adding a nucleotide sequence to the 3' end of the extension product. A non-limiting example of this process includes "tailing" with a single nucleotide (e.g., one of A, C, T, or G) using terminal tranferase and subsequent amplification using a primer that hybridizes to the tailed homopolymeric sequence. An example of such a method is described in Choi, Y. et al., *Cell,* 110:33-42 (2002). In some embodiments, this method is performed using demethylases comprising less than the full length DME protein sequences (or substantially identical sequences thereof) as disclosed herein or using chimeric demethylases (or substantially identical sequences thereof) as described herein. In some embodiments, the primer extension methods of the invention do not involving adding nucleotides to the extension product with a terminal transferase.

B. Methods Involving Covalent Bonding of Demethylase to DNA

The present invention also provides methods of detecting DNA methylation by taking advantage of the ability of the polypeptides of the invention to bind to methylated DNA. The demethylases of the invention temporarily bind to methylated DNA in the process of introducing a nick by cleavage of the phosphodiester backbone of DNA. This temporary binding of the DNA can be converted to a covalent bond if the demethylase and DNA are contacted together in the presence of a reducing agent. The presence of the reducing agent results ins a chemical reduction reaction resulting in covalent linkage of the demethylase to the DNA at the site of the methylated nucleotide. Exemplary non-limited reducing agents include $NaBH_4$.

Once the demethylase is covalently bound to the DNA, the DNA/demethylase complex can be separated from other DNA (and, e.g., protein, carbohydrates and other cellular constituents) in the sample using any agent that has affinity for the demethylase. For example, a reagent that specifically binds to the demethylase can be bound to a solid surface, the demethylase/DNA mixture can be contacted to the agent under conditions in which the agent binds to the demethylase and then washed, thereby removing any DNA not bound to the demethylase. Exemplary agents that bind the demethylases of the invention include, but are not limited to antibodies that bind the demethylases. In alternate embodiments, the demethylase can be engineered to include an epitope or other tag that is recognized by an affinity agent. For example, a poly-His sequence can be genetically engineered to either end of the demethylase. Nickel can then be used as an affinity agent to bind the poly-His demethylase bound to DNA. In another non-limiting embodiment, the demethylase is biotinylated and the affinity agent is streptavidin or another molecule with affinity for biotin. In yet another embodiment, an epitope tag is genetically engineered into the demethylase and an antibody that binds to the epitope is used to bind to the demethylase.

Once the demethylase/DNA complex is separated from non-bound DNA, the double stranded DNA strand bound to the demethylase is detected directly. Alternatively, the DNA bound to the demethylase is double stranded and the doubles-stranded DNA is denatured after the demethylase/DNA complex is separated from non-bound DNA, and the resulting intact strand of DNA is detected. Detection can include any nucleic acid detection method known in the art, e.g., nucleic acid amplification techniques such as those relying on PCR.

IV. Kits

For use in diagnostic, prognostic, research applications and other uses described herein, kits are also provided by the invention. The kits of the invention may comprise any or all of the reagents to perform the methods described herein. Such kits may include any or all of the following: at least one demethylase polypeptide of the invention, or nucleic acid encoding a demethylase, primers for primer extension (optionally detectably labeled), a DNA polymerase (optionally a thermostable polymerase capable of carrying out PCR under standard conditions), a terminal transferase, hybridization probes (optionally labeled) for detecting extension products, etc.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

V. Therapeutic Use of Demethylases

The present invention also provides for use of the demethylase polypeptides of the invention to reduce methylation in cells, including cells in vivo as well as ex vivo (e.g., cells extracted from an individual, treated with a demethylase and then returned to an individual). Thus, demethylases of the invention can be used for the purpose of modulating the activity of target genes through chromatin architecture in animal cells as well as plant cells. For example, in some embodiments, a demethylase of the invention is used to catalytically remove 5-MeC from target gene DNA in several ways: e.g., (1) by fusing the demethylase to a sequence specific DNA binding protein, or (2) by fusing the demethylase to a subunit of the target repressor complex such as MeCP2 or Sin3. When combined with cell, tissue, or developmentally specific promoters, a demethylase of the invention can be used to modulate specific sets of target genes.

In addition, reactive oxygen species, partially reduced species that are produced as intermediates of aerobic respiration, are powerful oxidizing agents that escape the mitochondria and attach via cellular components. Ionizing radiation and other agents that generate free radicals also produce reactive oxygen species that can attack the genome and cause lesions that are thought to have a key role in causing cancer and ageing. For example, 7,8-dihydro-8-oxoguanine (oxoG) is a very deleterious adduct generated by oxidation of the guanine base in DNA. The oxoG protein can pair with either cytosine or adenine during DNA replication. Thus, oxoG residues in DNA give rise to G/C to T/A transversion mutations. These transversions are common somatic mutations found in human cancers. Demethylases of the invention, such as those described herein, represent a defense against oxoG by catalysing the expulsion of the oxoG. Thus, in some embodiments, enhancing demethylase activity is a method to reduce the incidence of mutations in animal cells. Also, a demethylase of the invention can be used to catalytically remove oxoG from a target gene by fusing a demethylase of the invention to a sequence specific DNA binding protein. When combined with a cell, tissue, or developmentally specific promoters a demethylase of the invention can be used to modulate repair of target genes.

As described above, the polypeptides of the invention can be targeted to chromosomal regions of interest by linking the polypeptides of the invention, including fragments with demethylase activity, to a DNA-binding domain that binds a target sequence. For example, it is known that an enzyme that methylates DNA (Dam methylase) can be targeted to specific sites in the genome (B. V. Steensel and S. Henikoff, *Nature Biotechnology* 18:424-428 (2000)). Specifically, the methylase was tethered to the DNA-binding domain of GAL4. When recombinant GAL4-methylase protein was expressed in transgenic *Drosophila*, targeted methylation occurred in a region of a few kilobases surrounding the GAL4 DNA binding sequence. In a analogous fashion, a demethylase of the invention can be tethered (e.g., as a translational fusion or chemically linked) to proteins that interact at specific sites in the genome). As a result, specific targeted regions of the genome are hypomethylated by a demethylase of the invention. As discussed above, typically hypomethylation promotes transcription of genes (S. E. Jacobsen, *Current Biology* 9, 617 (1999). The invention provides compositions and methods for demethylation of a desired area of the chromosome by targeting a demethylase of the invention to those regions. Thus, these embodiments provide additional ways to activate transcription of a desired gene in a targeted chromosomal region.

EXAMPLES

The following examples are offered to illustrate, but not to limit the claimed invention.

Summary

DEMETER (DME) is a DNA glycosylase that excises 5-methylcytosine from DNA leading to active DNA demethylation. DME uniquely excises 5-methylcytosine in all sequence contexts. However, production of DME (full length and DMEΔN677) in *E. coli* is difficult because of its large size (1,729 amino acids) and poor solubility. As shown in FIG. 1, in this invention, we engineered DME by removing interdomain region 1 (IDR1) and replacing it with a small linker (lnk). The size of DMEΔN677ΔIDR1::lnk is only 38.9% of full-length DME, and its expression level in *E. coli* significantly increased. This improved both yield and solubility while preserving enzyme activity. When fused with different types of tags (e.g., 6×His (SEQ ID NO:15), maltose-binding protein, small ubiquitin-like modifier, glutathione S transferase, and thioredoxin) and produced in *E. coli*, DMEΔN677ΔIDR1::lnk was successfully expressed and highly soluble in all cases. His-tagged DMEΔN677ΔIDR1::lnk was successively purified over Nickel, Heparin, and Superdex 200 columns with improved stability and little degradation and/or truncation.

Introduction

DME is a DNA glycosylase that excises 5-methylcytosine from DNA (Gehring et al., 2006). DME is primarily expressed in the central cell of the female gametophyte in *Arabidopsis* and catalyzes female-specific DNA demethylation at target loci such as MEDEA, FWA, and FIS2 (Choi et al., 2002, Kinoshita et al., 2004, Jullien et al., 2006). Asymmetric DNA methylation between the paternal and maternal alleles is epigenetically inherited to the zygotic endosperm, where the less methylated maternal allele is expressed while the hypermethylated paternal allele silenced. Such monoallelic expression according to the parent-of-origin, that is called gene imprinting, is crucial for endosperm development and seed viability.

DME encodes a 1,729 amino acid peptide (Choi et al., 2002). A centrally located DNA glycosylase domain (1167-1368) contains a helix-hairpin-helix (HhH) motif. As an enzyme initiating the base excision repair (BER), the HhH motif in DME catalyzes excision of 5-methylcytosine, and the substitution of catalytic residues (K1286Q and D1304N) abolishes the enzyme activity (Gehring et al., 2006). In addition, DME has four cysteine residues adjacent to the DNA glycosylase domain that hold a [4Fe-4S] cluster in place. This cluster, found in many DNA glycosylases, is thought to play a role in DNA binding and/or structural stability. We found that site-directed mutagenesis on the residues comprising the [4Fe-4S] cluster disrupted 5-methylcytosine excision activity, proposing its necessity in DME function (U.S. patent application Ser. No. 12/006,779).

There are three other DME-like DNA glycosylases in *Arabidopsis* - ROS 1, DML2, and DML3 (Choi et al., 2002, Penterman et al., 2007). Besides the above mentioned DNA glycosylase domain, two additional conserved domains (Domain A and Domain B) are present in this family (FIG. 1). These domains flank the central DNA glycosylase domain. Even though their function is still elusive with no homology to other proteins, these domains are inevitable for DME activity, suggesting their essential role in excision of 5-methylcytosine. These conserved domains are connected with interdomain regions IDR1 and IDR2, the former is variable in size (395 amino acids for DME and 73 for DML3) while the latter comprises approximately 50 amino acids in all DME and DME-like proteins (FIG. 1). Unlike highly conserved glycosylase domain and Domains A and B, these IDR1 and IDR2 show little homology between the DME family members.

In the previous study, 537 amino acids at the N-terminus of DME were removed and fused with a maltose binding protein (MBP) for expression in *E. coli* (Gehring et al., 2006). This fusion protein MBP-DMEΔN537 specifically excised 5-methylcytosine from DNA in all sequence contexts (Gehring et al., 2006), suggesting that N-terminal 537 amino acids are dispensable for base excision activity. DMEΔN537 was soluble and active only when fused with MBP. However, the size of MBP-DMEΔN537 (1,587 amino acids; Mw=177.1 kDa) is still too big to be stably expressed at a high level in *E. coli*.

In this patent application, we report that engineered DME which has both a further N-terminal truncation and an internal IDR1 deletion displays improved yield, stability and solubility, while retaining essential 5-methylcytosine glycosylase activity.

Results

IDR1 of DMEΔN677 was removed and replaced with a short linker peptide (lnk) as shown in FIG. 1. At the same time, two unique restriction enzyme sites PstI and KpnI were incorporated at both 5'- and 3' ends of lnk for further manipulation at this region. This DMEΔN677ΔIDR1::lnk fragment consists of 673 amino acids with all three conserved domains preserved (FIG. 1). The size of DMEΔN677ΔIDR1::lnk is only 38.9% of full-length DME owing to the removal of both nonconserved N-terminal region and IDR1.

In order to test 5-methylcytosine excision activity, DMEΔN677ΔIDR1::lnk was fused with MBP and expressed in *E. coli*. The resulting MBP-DMEΔN677ΔIDR1::lnk was purified over an amylose resin and reacted with methylated DNA substrate as described by Gehring et al. (2006). As shown in FIG. 2, MBP-DMEΔN677ΔIDR1::lnk was able to excise 5-methylcytosine to the same extent with MBP-DMEΔN677. This implies that IDR1 is unnecessary for DME activity and that a connection of Domain A to a glycosylase domain via a short linker peptide does not affect the overall folding and assembly of the protein.

We next examined the expression of DMEΔN677ΔIDR1::lnk fused with different types of fusion proteins—6×His (SEQ ID NO:15), glutathione S-transferase (GST), small ubiquitin-like modifier (SUMO), MBP, and thioredoxin (Trx). DMEΔN677ΔIDR1::lnk was expressed at a higher level in E. coli than DMEΔN677 with no IDR1 deletion. In addition, unlike DMEΔN677 that was soluble only when fused with MBP, DMEΔN677ΔIDR1::lnk was soluble in all cases (FIG. 3). This suggests that a deletion of IDR1 improves both yield and solubility of the protein when expressed in E. coli.

Purification of MBP-DMEΔN677 barely reached >90% of purity due possibly to largely unstructured regions present in IDR1, which are often responsible for the instability of the protein. We fused DMEΔN677ΔIDR1::lnk with 6×His and expressed in E. coli. As shown in FIG. 4, 6×His (SEQ ID NO:15) tagged DMEΔN677ΔIDR1::lnk was successively purified over HisTrap, Heparin, and Superdex 200 columns with improved purity at each step. Much less amount of small molecular weight fragments was observed in the final stage of purification compared to DMEΔN677 (FIG. 4). Such small fragments might represent early-truncated expression or degradation of the protein. However, a deletion of IDR1 appears to stabilize the protein with minimal truncation or degradation problems. FIG. 5 summarizes the properties of DME, DMEΔN677, and DMEΔN677ΔIDR1::lnk.

Materials and Methods

Construction of c2x-DMEΔN677ΔIDR1::lnk

The DMEΔN677 sequence was cloned into the pMAL-c2x vector (NEB) at XbaI and SalI sites (c2x-DMEΔN677). Primers JH151 (5'-TGAAGAGCCATTACCACT TGA TCC TGC AGG AGG GAA TCG AGC AGC TAG-3' (SEQ ID NO:9)) and JH152 (5'-AGTGGTAATGGCTCTTCA GGA AAC GGT ACC AGC CAG TGG GAT AGT CTC-3'(SEQ ID NO:10)) were extended on the c2x-DMEΔN677 to create a linker sequence. The underlined sequences are complementary to each other. Following the treatment of DpnI to remove template DNA, the product was annealed and then PCR-amplified with primers JH-RNseqF (5'-CAG ATG TCC GCT TTC TGG TAT G-3' (SEQ ID NO:11)) and JH153 (5'-CAT ACA GTG TTC GTT GAT CGA G-3' (SEQ ID NO:12)) creating DMEΔN677ΔIDR1::lnk in which IDR1 is replaced with a short linker peptide (lnk, AGSSGNGSSGNG (SEQ ID NO:4)). The PCR product was digested with XbaI and XhoI and reinserted into the c2x-DMEΔN677 at the corresponding sites.

Construction of DMEΔN677ΔIDR1::lnk fusion with 6×His (SEQ ID NO:15), GST, SUMO, MBP, and Trx The c2x-DMEΔN677ΔIDR1::lnk plasmid was PCR-amplified with primers JH154 (5'-TTA AGG ATC CTA CAA AGG AGA TGG TGC AC-3' (SEQ ID NO:13)) and JH155 (5'-TTA AGT CGA CTT AGG TTT TGT TGT TCT TCA ATT TGC-3' (SEQ ID NO:14)). The product was digested with BamHI and SalI and then cloned into the following pET-19b (Novagen) derivatives at the corresponding sites: pBG100 (6×His), pBG101 (GST), pBG102 (SUMO), pLM302 (MBP), and pLM304 (Trx) (provided by Brandt Eichman at Vanderbilt University).

Production and Purification of DMEΔN677ΔIDR1:lnk

The c2x-DMEΔN677ΔIDR1::lnk plasmid was transformed into Rosetta2 cells (Novagen) for expression. The other constructs were transformed into Rosetta2 (DE3) cells (Novagen). Expression of DMEΔN677ΔIDR1::lnk was induced with IPTG at 18° C. for 5 hrs. MBP-DMEΔN677ΔIDR1::lnk was purified over an amylose resin (NEB). The other proteins were first purified using HisTrap FF (GE Healthcare) utilizing 6×His (SEQ ID NO:15) in the fusion peptide. The subsequent purifications over Heparin HP (GE Healthcare) and Superdex 200 (GE Healthcare) columns were done according to the manufacturer's protocol.

5-Methylcytsine Excision Assay

The in vitro 5-methylcytosine excision assay was done as described by Gehring et al. (2006).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated polypeptide consisting of:
   a first amino acid sequence, wherein the first amino acid sequence is at least 90% identical to the amino acid sequence of SEQ ID NO: 1,
   a second amino acid sequence, wherein the second amino acid sequence is at least 90% identical to the amino acid sequence of SEQ ID NO: 2, and
   optionally a linker, wherein the linker consists of 1-300 amino acids,
   wherein the first and second amino acid sequences are linked directly or by the linker and wherein the polypeptide excises methylated cytosines in DNA when contacted to DNA comprising methylated cytosines.

2. The polypeptide of claim 1, wherein the first and second amino acid sequences are linked directly.

3. The polypeptide of claim 1, wherein the first and second amino acid sequences are linked by the linker.

4. The polypeptide of claim 3, wherein the linker is heterologous to the first or second amino acid sequence.

5. The polypeptide of claim 3, wherein the linker consists of 10-300 amino acids of the amino acid sequence of SEQ ID NO: 3.

6. The polypeptide of claim 3, wherein the linker consists of 20 or fewer amino acids.

7. The polypeptide of claim 3, wherein the linker consists of the amino acid sequence of SEQ ID NO: 4.

8. The polypeptide of claim 1, wherein the first amino acid sequence is at least 95% identical to the amino acid sequence of SEQ ID NO: 1.

9. The polypeptide of claim 1, wherein the second amino acid sequence is at least 95% identical to the amino acid sequence of SEQ ID NO: 2.

10. The polypeptide of claim 1, wherein the first amino acid sequence consists of the amino acid sequence of SEQ ID NO: 1 and the second amino acid sequence consists of the amino acid sequence of SEQ ID NO: 2.

11. A method of making the polypeptide of claim 1, the method comprising, culturing an isolated cell under conditions to allow for expression of the polypeptide of claim 1, wherein the isolated cell comprises an expression cassette, the expression cassette comprising a promoter operably linked to a polynucleotide encoding the polypeptide of claim 1 thereby making the polypeptide of claim 1.

12. The method of claim 11, further comprising purifying the polypeptide.

13. The method of claim 11, wherein the cell is a eukaryotic cell.

14. The method of claim 13, wherein the cell is a yeast, fungal, mammalian or insect cell.

15. The method of claim 11, wherein the cell is a prokaryotic cell.

* * * * *